United States Patent [19]
Garger et al.

[11] Patent Number: 6,037,456
[45] Date of Patent: Mar. 14, 2000

[54] PROCESS FOR ISOLATING AND PURIFYING VIRUSES, SOLUBLE PROTEINS AND PEPTIDES FROM PLANT SOURCES

[75] Inventors: Stephen J. Garger; R. Barry Holtz; Michael J. McCulloch; Thomas H. Turpen, all of Vacaville, Calif.

[73] Assignee: Biosource Technologies, Inc., Vacaville, Calif.

[21] Appl. No.: 09/037,751

[22] Filed: Mar. 10, 1998

[51] Int. Cl.[7] .............................. C07K 1/14; C07K 1/36; A61K 35/78; C07H 1/08; C12N 7/02
[52] U.S. Cl. .................... 530/412; 530/379; 435/419; 435/239; 424/195.1; 536/128
[58] Field of Search .................................. 530/351, 370, 530/379, 387.1, 413, 414, 419, 412; 435/172.3, 419, 239; 930/141, 145, 190; 424/195.1; 536/1.11, 123.1, 128

[56] References Cited

U.S. PATENT DOCUMENTS

| | | | |
|---|---|---|---|
| 3,637,396 | 1/1972 | Hollo et al. | 426/51 |
| 4,130,553 | 12/1978 | Batley, Jr. et al. | 530/379 |
| 4,233,210 | 11/1980 | Koch | 530/379 |
| 4,250,197 | 2/1981 | Koch | 426/51 |
| 4,268,632 | 5/1981 | Wildman et al. | 435/232 |
| 4,289,147 | 9/1981 | Wildman et al. | 131/290 |
| 4,334,024 | 6/1982 | Johal | 435/232 |
| 4,347,324 | 8/1982 | Wildman et al. | 435/232 |
| 4,370,267 | 1/1983 | Lehnhardt et al. | 530/378 |
| 4,396,763 | 8/1983 | Tsuchiya et al. | 536/123 |
| 4,400,471 | 8/1983 | Johal | 435/232 |
| 4,885,248 | 12/1989 | Ahlquist | 435/172.3 |
| 5,077,390 | 12/1991 | Wu et al. | 530/370 |
| 5,173,410 | 12/1992 | Ahlquist | 435/91 |
| 5,301,694 | 4/1994 | Raymond et al. | 131/297 |
| 5,316,931 | 5/1994 | Donson et al. | 435/172.3 |
| 5,320,953 | 6/1994 | Hudson et al. | 435/69.4 |
| 5,466,788 | 11/1995 | Ahlquist et al. | 536/24.1 |
| 5,500,360 | 3/1996 | Ahlquist et al. | 435/172.3 |
| 5,589,367 | 12/1996 | Donson et al. | 435/172.3 |
| 5,602,242 | 2/1997 | Ahlquist et al. | 536/23.72 |
| 5,627,060 | 5/1997 | Ahlquist et al. | 435/172.3 |
| 5,811,654 | 9/1998 | Jaynes et al. | 800/205 |

OTHER PUBLICATIONS

Brakke, M., "Density Gradient Centrifugation and its Application to Plant Viruses", *Adv. Virus. Res.* 7:193–224 (1960) no month found.

Gooding et al., "A Simple Technique for Purification of Tobacco Mosaic Virus in Large Quantities", *Phytopathological Notes* 57:1285 (Nov. 1967).

Khan et al., "Accumulation of a sulphur–rich seed albumin from sunflower in the leaves of transgenic subterranean clover (Trifolium subterraneum L.)", *Transgenic Res.* 5:178–185 (1996) no month found.

Mason et al., "Expression of Norwalk virus capsid protein in transgenic tobacco and potato and its oral immunogenicity in mice", *Proc. Natl. Acad. Sci. USA* 93:5335–5340 (May 1996).

Turpen et al., "Malarial Epitopes Expressed on the Surface of Recombinant Tobacco Mosaic Virus", *BioTechnology* 13:53–57 (Jan. 1995).

Ma et al., *Science* 268:716–719 (May 1995).

*Primary Examiner*—Ralph Gitomer
*Assistant Examiner*—Marjorie A. Moran
*Attorney, Agent, or Firm*—Albert P. Halluin, Esq.; Thomas Gallegos, Esq.; Wallace Wu

[57] ABSTRACT

The present invention features a method for isolating and purifying viruses, proteins and peptides of interest from a plant host which is applicable on a large scale. Moreover, the present invention provides a more efficient method for isolating viruses, proteins and peptides of interest than those methods described in the prior art. In general, the present method of isolating viruses, proteins and peptides of interest comprises the steps of homogenizing a plant to produce a green juice, adjusting the pH of and heating the green juice, separating the target species, either virus or protein/peptide, from other components of the green juice by one or more cycles of centrifugation, resuspenion, and ultrafiltration, and finally purifying virus particles by such procedure as PEG-precipitation or purifying proteins and peptides by such procedures as chromatography and/or salt precipitation.

24 Claims, 2 Drawing Sheets

PROCESS FOR ISOLATING AND PURIFYING VIRUSES, SOLUBLE PROTEINS AND PEPTIDES FROM PLANT SOURCES

FIELD OF THE INVENTION

The present invention relates to a process for isolating and purifying viruses, soluble proteins and peptides produced in plants. More specifically, the present invention is applicable on a large scale.

BACKGROUND OF THE INVENTION

Plant proteins and enzymes have long been exploited for many purposes, from viable food sources to biocatalytic reagents, or therapeutic agents. During the past decade, the development of transgenic and transfected plants and improvements in genetic analysis have brought renewed scientific significance and economical incentives to these applications. The concepts of molecular plant breeding and molecular plant farming, wherein a plant system is used as a bioreactor to produce recombinant bioactive materials, have received great attention.

Many examples in the literature have demonstrated the utilization of plants or cultured plant cells to produce active mammalian proteins, enzymes, vaccines, antibodies, peptides, and other bioactive species. Ma et al. (*Science* 268: 716–719 (1995)) were the first to described the production of a functional secretory immunoglobulin in transgenic tobacco. Genes encoding the heavy and light chains of murine antibody, a murine joining chain, and a rabbit secretory component were introduced into separate transgenic plants. Through cross-pollination, plants were obtained to co-express all components and produce a functionally active secretory antibody. In another study, a method for producing antiviral vaccines by expressing a viral protein in transgenic plants was described (Mason et al., *Proc. Natl. Acad. Sci. U.S.A.* 93: 5335–5340 (1996)). The capsid protein of Norwalk virus, a virus causing epidemic acute gastroenteritis in humans was shown to self-assemble into virus-like particles when expressed in transgenic tobacco and potato. Both purified virus-like particles and transgenic potato tubers when fed to mice stimulated the production of antibodies against the Norwalk virus capsid protein. Alternatively, the production and purification of a vaccine may be facilitated by engineering a plant virus that carries a mammalian pathogen epitope. By using a plant virus, the accidental shedding of virulent virus with the vaccine is abolished, and the same plant virus may be used to vaccinate several hosts. For example, malarial epitopes have been presented on the surface of recombinant tobacco mosiac virus (TMV) (Turpen et al., *BioTechnology* 13:53–57 (1995)). Selected B-cell epitopes were either inserted into the surface loop region of the TMV coat protein or fused into the C-terminus. Tobacco plants after infection contain high titers of the recombinant virus, which may be developed as vaccine subunits and readily scaled up. In another study aimed at improving the nutritional status of pasture legumes, a sulfur-rich seed albumin from sunflower was expressed in the leaves of transgenic subterranean clover (Khan et al. *Transgenic Res.* 5:178–185 (1996)). By targeting the recombinant protein to the endoplasmic reticulum of the transgenic plant leaf cells, an accumulation of transgenic sunflower seed albumin up to 1.3% of the total extractable protein could be achieved.

Work has also been conducted in the area of developing suitable vectors for expressing foreign genetic material in plant hosts. Ahlquist, U.S. Pat. No. 4,885,248 and U.S. Pat. No. 5,173,410 described preliminary work done in devising transfer vectors which might be useful in transferring foreign genetic material into plant host cells for the purpose of expression therein. Additional aspects of hybrid RNA viruses and RNA transformation vectors are described by Ahlquist et al. in U.S. Pat. Nos. 5,466,788, 5,602,242, 5,627,060 and 5,500,360 all of which are herein incorporated by reference. Donson et al., U.S. Pat. No. 5,316,931 and U.S. Pat. No. 5,589,367, herein incorporated by reference, demonstrate for the first time plant viral vectors suitable for the systemic expression of foreign genetic material in plants. Donson et al. describe plant viral vectors having heterologous subsenomic promoters for the systemic expression of foreign genes. The availability of such recombinant plant viral vectors makes it feasible to produce proteins and peptides of interest recombinantly in plant hosts.

Elaborate methods of plant genetics are being developed at a rapid rate and hold the promise of allowing the transformation of virtually every plant species and the expression of a large variety of genes. However, in order for plant-based molecular breeding and farming to gain widespread acceptance in commercial areas, it is necessary to develop a cost-effective and large-scale purification system for the bioactive species produced in the plants, either proteins or peptides, especially recombinant proteins or peptides, or virus particles, especially genetically engineered viruses.

Some processes for isolating proteins, peptides and viruses from plants have been described in the literature (Johal, U.S. Pat. No. 4,400,471, Johal, U.S. Pat. No. 4,334,024, Wildman et al., U.S. Pat. No. 4,268,632, Wildman et al., U.S. Pat. No. 4,289,147, Wildman et al., U.S. Pat. No. 4,347,324, Hollo et al., U.S. Pat. No. 3,637,396, Koch, U.S. Pat. 4,233,210, and Koch, U.S. Pat. No. 4,250,197, the disclosure of which are herein incorporated by reference). The succulent leaves of plants, such as tobacco, spinach, soybeam, and alfalfa, are typically composed of 10–20% solids, the remaining fraction being water. The solid portion is composed of a water soluble and a water insoluble portion, the latter being predominantly composed of the fibrous structural material of the leaf. The water soluble portion includes compounds of relatively low molecular weight (MW), such as sugars, vitamins, alkaloids, flavors, amino acids, and other compounds of relatively high MW, such as nature and recombinant proteins.

Proteins in the soluble portion of the plant bombast can be further divided into two fractions. One fraction comprises predominantly a photosynthetic protein, ribulose 1,5-diphosphate carboxylase (or RuBisCO), whose subunit molecular weight is about 550 kD. This fraction is commonly referred to as "Fraction 1 protein." RuBioCO is abundant, comprising up to 25% of the total protein content of a leaf and up to 10% of the solid matter of a leaf. The other fraction contains a mixture of proteins and peptides whose subunit molecular weights typically range from about 3 kD to 100 kD and other compounds including sugars, vitamins, alkaloids, flavors, amino acids. This fraction is collectively referred to as "Fraction 2 proteins." Fraction 2 proteins can be native host materials or recombinant materials including proteins and peptides produced via transaction or transgenic transformation. Transfected plants may also contain virus particles having a molecular size greater than 1,000 kD.

The basic process for isolating pant proteins generally begins with disintegrating leaf bombast and pressing the resulting pulp to produce "green juice". The process is typically performed in the presence of a reducing agent or antioxidant to suppress unwanted oxidation. The green juice, which contains various protein components and finely particulate green pigmented material, is pH adjusted and heated. The typical pH range for the green juice after adjustment is between 5.3 and 6.0 This range has been optimized for the isolation of Fraction 1 protein (or ribulose 1,5-diphosphate carboxylase). Heating, which causes the coagulation of green pigmented material, is typically controlled near 50° C. The coagulated green pigmented material can then be removed by moderate centrifugation to yield "brown juice." The brown juice is subsequently cooled and stored at a temperature at or below room temperature. After an extended period of time, e.g. 24 hours, ribulose 1,5-diphosphate carboxylase is crystallized from the brown juice. The crystallized Fraction 1 protein can subsequently be separated from the liquid by centrifugation. Fraction 2 proteins remain in the liquid, and they can be purified upon further acidification to a pH near 4.5. Alternatively, the crystal formation of ribulose 1,5-diphosphate carboxylase from brown juice can be effected by adding sufficient quantities of polyethylene glycol (PEG) in lieu of cooling.

The basic process for isolating virus particles is described in Gooding et al. (*Phytophathological Notes* 57:1285 (1967), the teaching of which are herein incorporated by reference). To purify Tobacco Mosaic Virus (TMV) from plant sources in large quantities, infected leaves are homogenized and n-butanol is then added. The mixture is then centrifuged, and the virus is retained in the supernatant. Polyethylene glycol (PEG) is then added to the supernatant followed by centrifugation. The virus can be recovered from the resultant PEG pellet. The virus can be further purified by another cycle of resuspension, centrifugation and PEG-precipitation.

Existing protocols for isolating and purifying plant viruses and soluble proteins and peptides, however, present many problems. First, protein isolation from plant sources have been designed in large part for the recovery of Fraction 1 protein, not for other biologically active soluble protein components. The prior processes for large-scale extraction of F1 proteins was for production of protein as an additive to animal feed or other nutritional substances. Acid-precipitation to obtain Fraction 2 proteins in the prior art is not effective, since most proteins denature in the pellet form. This is especially troublesome for isolating proteins and peptides produced by recombinant nucleic acid technology, as they may be more sensitive to being denatured upon acid-precipitation. Second, the existing methods of separation rely upon the use of solvents, such as n-butanol, chloroform, or carbon tetrachloride to eliminate chloroplast membrane fragments, pigments and other host related materials. Although useful and effective for small-scale virus purification, using solvents in a large-scale purification is problematic. Such problems as solvent disposal, special equipment designs compatible with flammable liquids, facility venting, and worker exposure protection and monitoring are frequently encountered. There are non-solvent based, small-scale virus purification methods, but these are not practical for large scale commercial operations due to equipment and processing limitations and final product purity (Brakke *Adv. Virus Res.* 7:193–224 (1960) and Brakke et al. *Virology* 39: 516–533 (1969)). Finally, the existing protocols do not allow a streamline operation such that the isolation and purification of different viruses, proteins and peptides can be achieved with minimum modification of a general purification procedure.

There is a need in the art for an efficient, non-denaturing and solvent-limited large-scale method for virus and soluble protein isolation and purification. This need is especially apparent in cases where proteins and peptides produced recombinantly in plant hosts are to be isolated. The properties of these proteins and peptides are frequently different from those of the native plant proteins. Prior art protocols are not suitable to isolate recombinant proteins and peptides of interest. In addition, the vast diversity of recombinant proteins and peptides from plants and the stringent purity requirement for these proteins and peptides in industrial and medical application requires an efficient and economical procedure for isolating and purifying them. Efficient virus isolation is also of great importance because of the utility of viruses as transaction vectors and vaccines. In some situations, proteins and peptides of interest may be attached to a virus or integrated with native viral proteins (fusion protein), such that isolating the protein or peptide of interest may in fact comprise isolating the virus itself.

SUMMARY OF THE INVENTION

The present invention features a method for isolating and purifying viruses, proteins and peptides of interest from a plant host which is applicable on a large scale. Moreover, the present invention provides a more efficient method for isolating viruses, proteins and peptides of interest than those methods described in the prior art.

In general, the present method of isolating viruses, proteins and peptides of interest comprises the steps of homogenizing a plant to produce a green juice, adjusting the pH of and heating the green juice, separating the target species, either virus or protein/peptide, from other components of the green juice by one or more cycles of centrifugation, resuspenion, and ultrafiltration, and finally purifying virus particles by such procedure as PEG-precipitation or purifying proteins and peptides by such procedures as chromoatgraphy, including affinity-based methods, and/or salt precipitation.

In one embodiment, the green juice is pH adjusted to a value of between about 4.0 and 5.2 and heated at a temperature of between about 45–50° C. for a minimum of about one min. This mixture is then subjected to centrifugation. The supernatant produced thereby contains virus if transfected and Fraction 2 proteins including recombinant products. Fraction 2 proteins may be separated from the pelleted Fraction 1 protein and other host materials by moderate centrifugation. Virus particles and Fraction 2 proteins may then be further purified by a series of ultrafiltration, chromatography, salt precipitation, and other methods, including affinity separation protocols, which are well known in the art. One of the major advantages of the instant invention is that it allows Fraction 2 proteins to be subjected to ultrafiltration whereas prior methods do not.

In a second embodiment, after pH and heat treatment, the pellet from centrifugation containing the virus, Fraction 1 protein and other host materials is resuspended in a water or buffer solution and adjusted to a pH of about 5.0–8.0. The mixture is subjected to a second centrifugation. The resuspension allows the majority of virus to remain in the supernatant after the second centrifugation and Fraction 1 protein and other host materials may be found in the resulting pellet. The virus particles may be further purified by PEG-precipitation or ultrafiltration if necessary prior to PEG-precipitation.

In a third embodiment, the coat protein of a virus is a fusion protein, wherein the recombinant protein or peptide of interest is integrated with the coat protein of a virus. During virus replication or during the process of virus isolation and purification, its coat protein may become detached from the virus genome itself, or accumulate as unassembled virus coat protein or the coat fusion may never be incorporated. After centrifugation of the pH adjusted and heated green juice, the pellet may contain the virus, unassembled fusion proteins, Fraction 1 protein, and other host materials. The pellet is then resuspended in water or a buffer solution and adjusted to a pH about 2.0–4.0 followed by a second centrifugation. The protein will remain in the resulting supernatant. The unassembled protein may be further purified according to conventional methods including ultrafiltration, salt precipitation, affinity separation and chromatography. The peptide or protein of interest may be obtained by chemical cleavage of the fusion protein. Such procedures are well known to those skilled in the art.

In a fourth embodiment, sugars, vitamins, alkaloids, flavors, and amino acids from a plant may also be conveniently isolated and purified. After centrifugation of the pH adjusted and heated green juice, the supernatant contains the Fraction 2 proteins, viruses and other materials, such as sugars, vitamins, alkaloids, and flavors. The supernatant produced thereby may be separated from the pelleted Fraction 1 protein and other host materials by moderate centrifugation. Sugars, vitamins, alkaloids, and flavors may then be further purified by a series of methods including ultrafiltration and other methods, which are well known in the art.

In a fifth embodiment, the present invention features viruses, proteins, peptides, sugars, vitamins, alkaloids, and flavors of interest obtained by the procedures described herein.

DETAILED DESCRIPTION OF THE INVENTION

The present invention features a novel method for isolating and purifying viruses, proteins and peptides of interest from a plant host. Moreover, the present invention provides a more efficient method for isolating viruses, proteins and peptides of interest than those methods described in the prior art. In addition, the present method is applicable on a large production scale.

In general, the present method of isolating viruses, proteins and peptides of interest comprises the steps of homogenizing a plant to produce a green juice, adjusting the pH of and heating the green juice, separating the target species, either virus or protein/peptide, from other components of the green juice by one or more cycles of centrifugation, resuspension, and ultrafiltration, and finally purifying virus particles by such procedure as PEG-precipitation or purifying proteins and peptides by such procedures as chromatography, including affinity separation, and/or salt precipitation.

Figure 1:
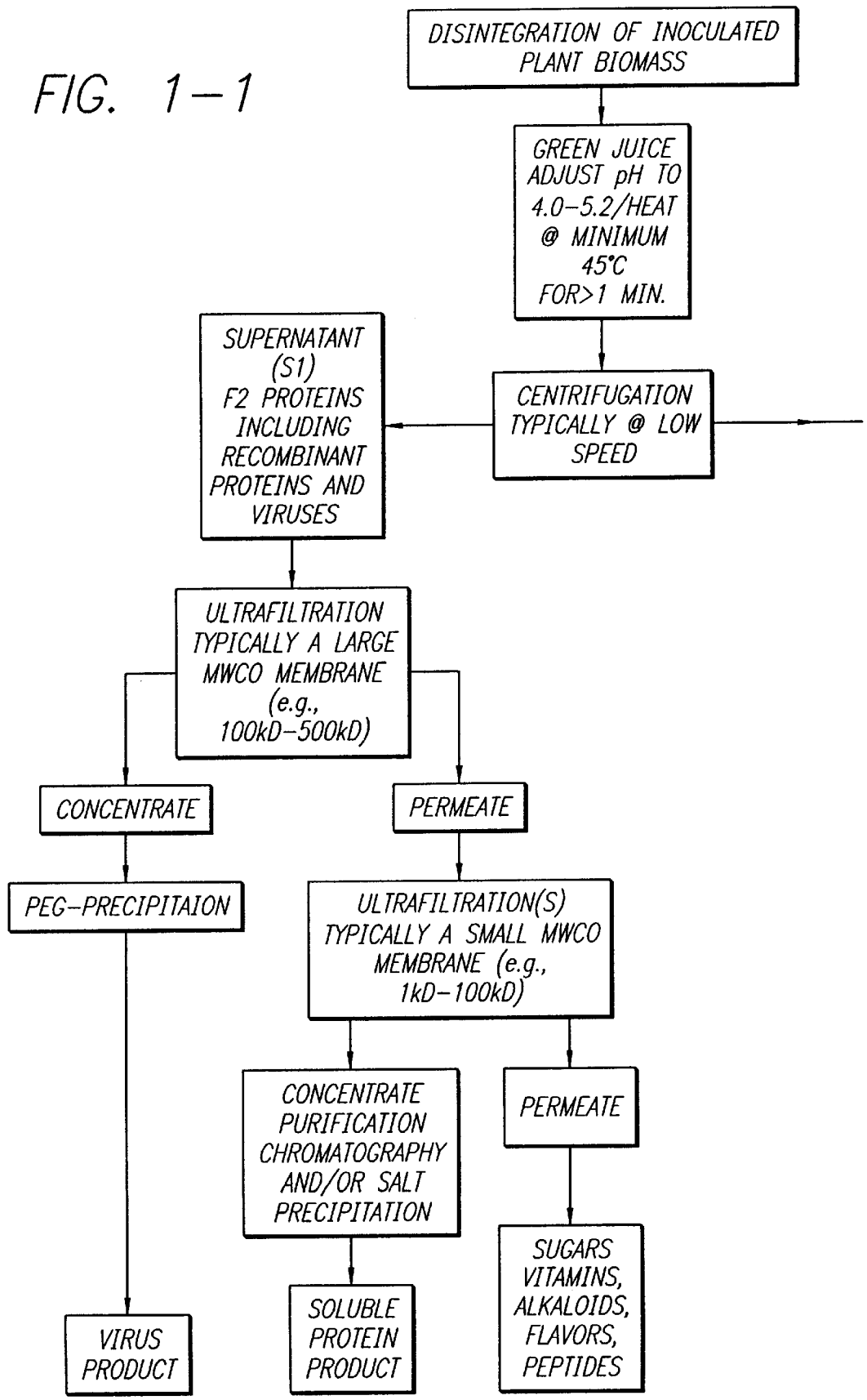
FIG. 1 represents a flow chart which demonstrates the present method for isolating and purifying viruses and soluble proteins and peptides from plant sources.
Figures 1, 2:
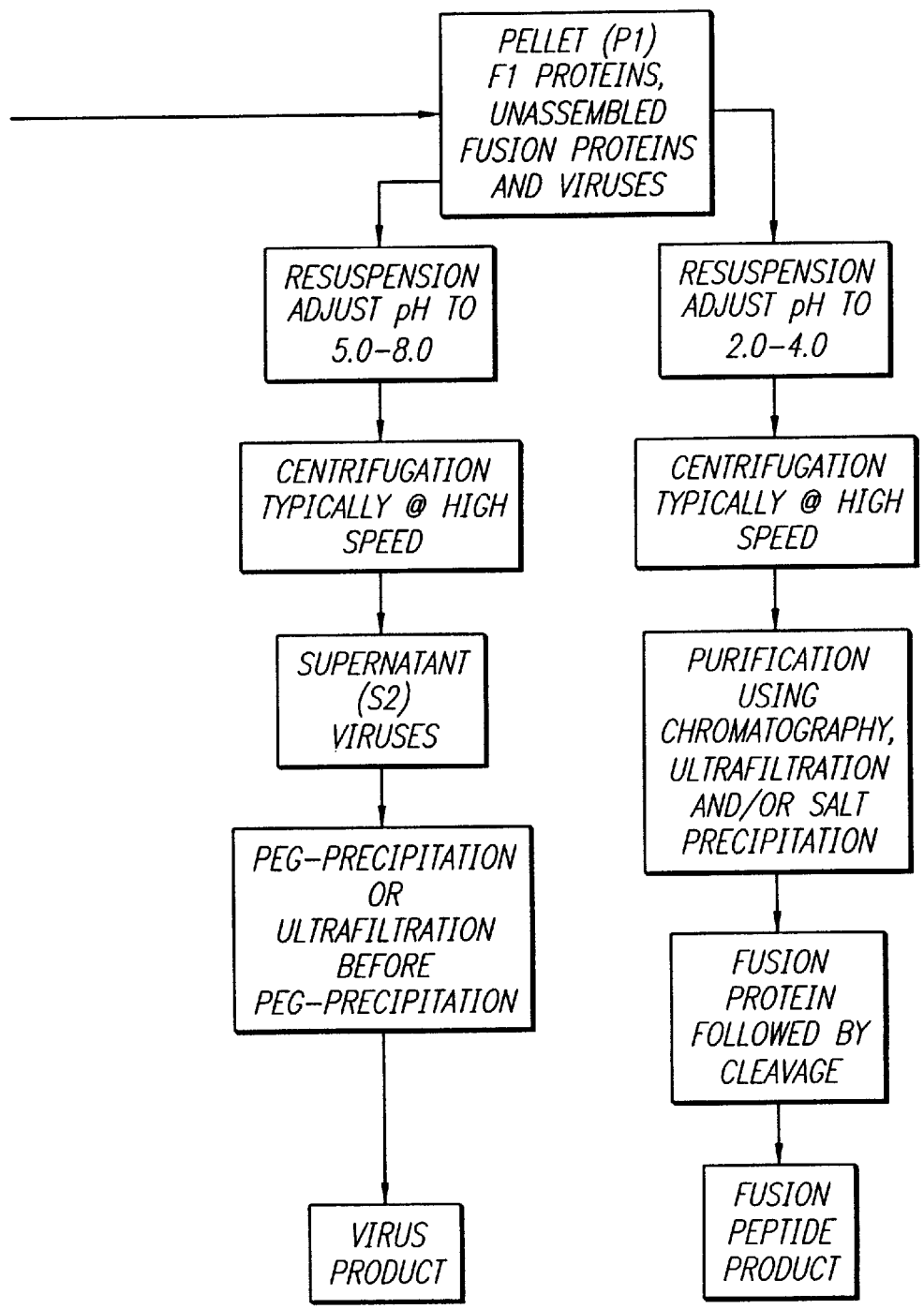

An illustration of the instant invention is presented in FIG. 1. However, this figure is intended merely to visualize the present invention and is not to be construed as being limiting to the procedures or orders of their appearances depicted therein. Any modifications of the instant invention which are functionally equivalent to the procedures and conditions disclosed herein are within the scope of the instant invention.

The initial step of the present method features homogenizing the subject plant. Plant leaves may be disintegrated using any appropriate machinery or process available. For instance, a Waring blender for a small scale or a Reitz disintegrator for a large scale has been successfully used in some embodiments of the instant invention. The homogenized mixture may then be pressed using any appropriate machinery or process available. For example, a screw press for a large scale or a cheesecloth for a small scale has been successfully employed in some embodiments of the instant invention. The homogenizing step may be performed in the presence of a suitable reducing agent or oxidizing agent to suppress unwanted oxidation. Sodium metabisulfite ($Na_2S_2O_5$) is successfully used in some embodiments of the instant invention. The subsequent steps to isolate and purify viruses and soluble proteins peptides may be performed generally according to the following procedures.

pH Adjustment and Heat Treatment of Green Juice

According to the present invention, the pH of the initial green juice is adjusted to a value less than or equal to 5.2 and then heated at a minimum temperature of about 45° C. In preferred embodiments of the instant invention, the green juice is pH adjusted to between about 4.0 and 5.2 and is then heated to a temperature of between about 45–50° C. for a minimum of one minute. In some embodiments of the instant invention, heat treatment between 10 to 15 minutes has been used successfully. Those skilled in the art will readily appreciate that the time allocated for heat treatment will vary depending on the recovery of the described species. Therefore, following pH adjustment, the heating time may vary from about one minute to over 15 minutes. Heat may be applied in any suitable manner, and the invention is not intended to be limiting in this regard. Those skilled in the art will appreciate that pH may be adjusted using many suitable acids or bases well known in the art. In some embodiments of the present invention, phosphoric acid has proven effective. The pH of green juice influences for distribution of virus, proteins and peptides in the supernatant or pellet during subsequent centrifugations. An optimal value for the target species may be obtained by testing the isolation and purification of the virus and or protein or peptide of interest on a small scale. Methods previously described in the literature for non-virus purification adjust the pH of the green juice to a value between 5.3 and 6.0 and use heat treatment of at a temperature of about 48–52° C.

The heat-treated and pH adjusted green juice is quite unique in that the pH of green juice influences the distribution of virus, proteins and peptides in the supernatant or pellet during subsequent centrifugations. Depending on the species of interest, the pH of green juice may be readily controlled to facilitate the isolation and purification of the desirable product, either virus particles or proteins and peptides. It thus provides a streamlined operation such that the isolation and purification of different viruses and proteins and peptides can be optimized with small modifications of a general purification procedure. Such modifications are within the routine skill of skilled artisans and do not require undue experimentation. The unique characteristic of green juice has enabled it to be processed in a variety of purification steps described below.

Centrifugation of Green Juice

The pH- and heat-treated green juice may then be subjected to centrifugation. Those of skill in the art may readily determine suitable conditions for centrifugation, including time interval and G-force. It is generally contemplated that centrifugation should be of sufficient G-force and time to pellet substantially all of Fraction 1 protein, chloroplast and other host materials, while retaining the desired target species in the supernatant fraction or at a sufficient speed and time to pellet the target species with Fraction 1 protein, chloroplast and other host materials. For example, centrifugation at 3000×G for two minutes or at 6000×G for three minutes have been effectively applied to the green juice in some embodiments of the instant invention. According to the present invention, a majority of Fraction 1 protein, unassembled fusion proteins and peptides, chloroplast and other host materials are pelleted (P1) by centrifugation, while Fraction 2 proteins including recombinant proteins and peptides may generally remain in the supernatant (S1) after this centrifugation (see FIG. 1). The virus, however, may partition between pellet and supernatant after centrifugation, depending upon the pH of the green juice the virus species, virus nucleic acid construct, plant species, plant age, and source of plant tissue, among other factors. At a low pH, preferably below a pH of about 5.0, the virus is predominantly retained in the pellet (P1). At a pH of between about 5.0 and 5.2, virus is present in the supernatant (S1) as well. Depending on the species of interest, the pH of green juice and subsequent centrifugation conditions may be readily controlled to facilitate the isolation and purification of the desirable product, either virus particles or proteins and peptides. Thus, the instant process provides a streamlined operation such that the isolation and purification of different viruses and proteins and peptides can be achieved with small modifications of a general purification procedure, which modifications require no undue experimentation for those of ordinary skill in the art.

Resuspension of Pellet in a pH Controlled Buffer

The pellet obtained by centrifugation of the pH-adjusted and heated green juice typically contains Fraction 1 protein, unassembled fusion proteins and peptides, viruses, and other host materials. It may be resuspended in water or in a buffer solution having the desired pH range, or pH adjusted to that range. The optimal pH is determined by the final species of interest. In some preferred embodiments, the pH range of resuspension is about 5.0 to 8.0 for isolating and purifying virus particles (see FIG. 1). In other embodiments, the pH range of resuspension is about 2.0 to 4.0 if the desired product is a fusion proteins/peptide (see FIG. 1). Those skilled in the art may readily choose appropriate buffer solution or acids or bases to reach the designed pH range without undue experimentation. Depending upon the percentage of solids of the pellet formed as a result of the first centrifugation procedure, a resuspension volume can be adjusted to a fraction of the starting green juice volume, typically in amounts of 10 to 100-fold of the original green juice volume.

Isolation and Purification of Virus

Viruses can be recovered from either the pellet (P1) alone, the supernatant (S1), or both the supernatant (S1) and pellet (P1) after centrifugation of the green juice depending upon the pH and degree of virus partitioning.

When the pH of green juice is adjusted to a low value, for example, about 4.0, the virus is in general quantitatively retained in the pellet along with Fraction 1 protein chloroplast and other host material after centrifugation of the green juice (see FIG. 1). After resuspension in a solution having a pH of about 5.0 to 8.0, the mixture may be subjected to another centrifugation step. Virus particles are predominantly retained in the supernatant (S2) and may be separated from Fraction 1 protein, chloroplast fragments and other host materials in the pellets. Usually only about 5–10% of the starting green juice protein remains in S2. The virus containing supernatant may then be ultrafiltered, if necessary, using a molecular weight cut-off (MWCO) in the range of about 1–500 kD membrane according to any one of the ultrafiltration techniques known to those of skill in the art. For example, a 100 kD MWCO membrane has been successfully used in some embodiments of the instant invention to retain virus particles in the concentrates, while smaller protein components filter through. The ultrafiltration step results in a substantial further reduction in the process volume. In some embodiments, further reductions in the process volume of 1- to 30-fold or greater are attainable. From ultrafiltration or centrifugation, a final purification of virus may be accomplished by prior art methods such as PEG-precipitation, centrifugation, resuspension, and clarification.

In some embodiments of the instant invention, virus particles may also be obtained from the supernatant (S1) after the centrifugation of the green juice. This supernatant fraction normally contains Fraction 2 proteins and peptides (see FIG. 1). In some embodiments of the instant invention, the pH of green juice may be adjusted to a value between about 5.0 and 5.2, preferably around pH 5.0. A significant portion of virus particles may then be recovered from the supernatant (S1) in addition to the pellet (P1) after centrifugation of the green juice. The virus containing supernatant may be ultrafiltered including, if necessary, diafiltration using a molecular weight cut-off membrane in the range of about 1–500 kD according to any one of the ultrafiltration and diafiltration techniques known to those skilled in the art. For example, a 100 kD MWCO membrane has been successfully used in some embodiments of the instant invention to retain virus particles in the concentrates, while smaller protein components, e.g. Fraction 2 proteins filter through. The ultrafiltration step results in a substantial further reduction in the process volume. From ultrafiltration or centrifugation, a final purification of virus may be accomplished by prior art methods such as PEG-precipitation, centrifugation, resuspenion, and clarification.

An isolation and purification procedure according to the methods described herein has been used to isolate TMV-based viruses from three tobacco varieties (Ky8959, Tn86 and MD609) and *Nicotiana benthamiana*. A number of TMV-based viruses have been obtained Figure including, TMV204 (wild type, SEQ ID NO:1:), TMV261 (coat protein read-throughs, SEQ ID. NO:2:), TMV291 (coat protein loop fusion, SEQ ID NO.:3:), TMV811 (SEQ ID NO:4:), and TMV861 (coat protein read throughs, SEQ ID NO.:5:). TMV 261 and TMV291 have been shown to be unstable during some isolation procedures, yet remain intact during the present procedure. These viral vectors are used merely as examples of viruses that can be recovered by the instant invention and are not intended to limit the scope of the invention. A person of ordinary skill in the art will be able to use the instant invention to recover other viruses. The virus of interest may be a potyvirus, a tobamovirus, a bromovirus, a armovirus, a luteovirus, a marafivirus, the MCDV group, a necrovirus, the PYFV group, a sobemovirus, a tombusvirus, a tymovirus, a capillovirus, a closterovirus, a carlavirus, a potexvirus, a comovirus, a dianthovirus, a fabavirus, a repovirus, a PEMV, a furovirus, a tobravirus, an AMV, a tenuivirus, a rice necrosis virus, caulimovirus, a geminivirus, a reovirus, the commelina yellow mottle virus group and a cryptovirus, a Rhabovirus, or a Bunyavirus.

The present methods of isolating and purifying virus particles represent significant advantages over the prior art methods. They allow the ultrafiltration of virus-containing supernatant (S1 and/or S2), which significantly reduces the processing volume and removes plant components, such as, sugars, alkaloids, flavors, and pigments and Fraction 1 and 2 proteins. Desired virus particles can be enriched as particulate. The concentration and purification of virus particles is thus rapid and effective.

Isolation and Purification of Soluble Proteins and Peptides

The Fraction 2 proteins including recombinant proteins and peptides remain soluble after pH adjustment and heat treatment and centrifugation of green juice (see FIG. 1). The Fraction 2 protein-containing supernatant has removed sufficient Fraction 1 proteins, chloroplast and other host materials, to enable an efficient isolation and purification of Fraction 2 proteins, especially recombinant proteins and peptides, using size fractionation by ultrafiltration, concentration and diafiltration. Ultrafiltration is typically performed using a MWCO membrane in the range of about 1 to 500 kD according to methods well known in the art. In some embodiments of the instant invention, a large MWCO membrane is first used to filter out the residual virus and other host materials. Large molecular weight components may remain in the concentrates. Filtrates containing the proteins/peptides of interest may be optionally passed through another ultrafiltration membrane, typically of a smaller MWCO, such that the target compound can be collected in the concentrates. Additionally cycles of ultrafiltration may be conducted, if necessary, to improve the purity of the target compound. The choice of MWCO size and ultrafiltration conditions depends on the size of the target compound and is an obvious variation to those skilled in the art. The ultrafiltration step generally results in a reduction in process volume of about 10- to 30-fold or more and allows diafiltration to further remove undesired molecular species. Finally, proteins or peptides of interest may be purified using standard procedures such as chromatography, salt precipitation, solvent extractions including super critical fluids such as $CO_2$ and other methods known to those of skill in the art.

The present isolation procedure has been used to successfully isolate and concentrate secretory IgA antibody and α-trichosanthin. The invention is also specifically intended to encompass embodiments wherein the peptide or protein of interest is selected from the group consisting of IL-1, IL-2, IL-3, IL-4, IL-5, IL-6, -IL-7, IL-8, IL-9, IL-10, IL-11, IL-12, EPO, G-CSF, GM-CSF, hPG-CSF, M-CSF, Factor VIII, Factor IX, tPA, receptors, receptor antagonists, antibodies, single-chain antibodies, enzymes, neuropolypeptides, insulin, antigens, vaccines, peptide hormones, calcitonin, and human growth hormone. In yet other embodiments, the soluble protein or peptide of interest may be an antimicrobial peptide or protein consisting of protegrins, magainins, cecropins, melittins, indolicidins, defensins, β-defensins, cryptdins, clavainins, plant defensins, nicin and bacterecins. These and other proteins and peptides of interest may be naturally produced or produced by recombinant methodologies in a plant.

The present method of isolating and purifying Fraction 2 proteins represents significant advantages from the prior art methods. First, it does not require acid-precipitation of F2 proteins. Acid-precipitation in the prior art may not be described since many proteins may be denatured or lose enzymatic or biological activity. Fraction 2 proteins including recombinant proteins and peptides in the instant invention are not retained in a pellet form, thereby minimizing the risk of protein denaturation. The present method thereby minimizes denaturation of proteins and peptides of interests. Second, because the more abundant component, Fraction 1 protein, is eliminated during the early stages of purification, the downstream process allows the ultrafiltration of Fraction 2 proteins. Ultrafiltration of Fraction 2 proteins permits significant reduction of processing volume and allows rapid concentration and purification of proteins and peptides. Desirable proteins and peptides can be enriched by molecular weight. Rapid concentratin and purification also reduces or eliminates the degradation or denaturation due to endogenous protease activities. Ultrafiltration of Fraction 2 proteins is not applicable with methods in the prior art. Finally, the concentration of Fraction 2 proteins including recombinant proteins and peptides requires no solvents and no additional chemicals. Plant protein and peptide isolation procedures in the prior art frequently use solvents such as n-butanol, chloroform, and carbon tetrachloride to eliminate chloroplast membrane fragments, pigments and other host related materials. Such methods are not easily practiced on a large and commercially valuable scale since these methods present the problems of safety and solvent disposal, which often require designing special equipment compatible with flammable fluids, and hence require facility venting and providing protective equipment to workers.

Isolation and Purification of Unassembled Fusion Proteins and Fusion Peptides

During virus replication or during the process of isolating and purifying a virus, its coat protein may become detached from the virus genome itself, or accumulate as unassembled virus coat protein, or the coat protein may never be incorporated. One of ordinary skill in the art can invision that the coat protein can be designed through established recombinant nucleic acid protocols to intentionally be unassembled for commercial recovery of proteins having a plurality of biochemical features. This coat protein may contain a recombinant component integrated with the native coat protein, or fusion proteins. These unassembled fusion proteins typically co-segregate in the pellet (P1) with Fraction 1 protein after centrifugation of pH adjusted and heated green juice (see FIG. 1). The pellet may then be resuspended in water or in a buffer with a pH value within the range of about 2.0 to 4.0 followed by another centrifugation. The unassembled protein may be further purified according to conventional methods including a series of ultrafiltration, centrifugation and chromatography steps. The fusion peptide may be obtained followed by chemical cleavage of the desired peptide or protein from the fusion peptide (fusion proteins). Such procedures are well known to those skill in the art.

The present invention procedure has been used to successfully isolate and concentrate α-amylase-indolicidin fusion protein. The invention is also specifically intended to encompass embodiments wherein the fusion protein or peptide may contain a peptide or protein selected from the group consisting of IL-1, IL-2, IL-3, IL-4, IL-5, IL-6, IL-7, I1-8, IL-9, IL-10, IL-11, IL-12, EPO, G-CSF, GM-CSF, hPG-CSF, MCSF, Factor VIII, Factor IX, tPA, receptors receptor antagonists, antibodies, single-chain antibodies, enzymes, neuropolypeptides, insulin, antigens, vaccines, peptide hormones, calcitonin, and human growth hormone. In yet other embodiments, the protein or peptide present in the fusion protein or peptide may be an antimicrobial peptide or protein consisting of protegrins, magainins, cecropins, melittins, indolicidins, defensins, β-defensins, cryptdins, clavainins, plant defensins, nicin and bactenecins.

Isolation and Purification of Sugars, Vitamins, Alkaloids, and Flavors

Sugars, vitamins, alkaloids, flavors, amino acids from a plant may also be conveniently isolated and purified using the method of the instant invention. After centrifugation of the pH adjusted and heated green juice, the supernatant contains the Fraction 2 proteins, viruses and other materials, including sugars, vitamins, alkaloids, and flavors. The supernatant produced thereby may be separated from the pelleted Fraction 1 protein and other host materials by centrifugation. Sugars, vitamins, alkaloids, flavors may then be further purified by a series of low molecular weight cutoff ultrafiltration and other methods, which are well known in the art.

Definitions

In order to provide an even clearer and more consistent understanding of the specification and the claims, including the scope given herein to such terms, the following definitions are provided:

A "virus" is defined herein to include the group consisting of a virion wherein said virion comprises an infectious nucleic acid sequence in combination with one or more viral structural proteins; a non-infectious virion wherein said non-infectious virion comprises a non-infectious nucleic acid in combination with one or more viral structural proteins; and aggregates of viral structural proteins wherein there is no nucleic acid sequence present or in combination with said aggregate and wherein said aggregate may include virus-like particles (VLPs). Said viruses may be either naturally occurring or derived from recombinant nucleic acid techniques and include any viral-derived nucleic acids that can be adopted whether by design or selection, for replication in whole plant, plant tissues or plant cells.

A "virus population" is defined herein to include one or more viruses as defined above wherein said virus population consists of a homogeneous selection of viruses or wherein said virus population consists of a heterogenous selection comprising any combination and proportion of said viruses.

"Virus-like particles" (VPLs) are defined herein as self-assembling structural proteins wherein said structural proteins are encoded by one or more nucleic acid sequences wherein said nucleic acid sequence(s) is inserted into the genome of a host viral vector.

"Protein and peptides" are defined as being either naturally-occurring proteins and peptides or recombinant proteins and peptides produced via transfection or transgenic transformation.

EXAMPLES

The following examples further illustrate the present invention. These examples are intended merely to be illustrative of the present invention and are not to be construed as being limiting. The examples are intended specifically to illustrate recoveries of virus, protein and peptide of interest which may be attained using the process within the scope of the present invention.

Example 1

Fraction 1 Protein Pelleted From Green Juice at Low pH

A tobacco plant of variety of MD609 was inoculated 27 days after sowing with TMV 811. Forty days after inoculation, the plant was harvested. Leaf and stalk tissue (150 g) were combined with 0.04% sodium metabisulfite solution (150 ml) in a 1-L Waring blender. The plant tissue was ground on high speed for a period of two minutes. The resulting homogenate was pressed through four layers of cheesecloth, and the pressed fiber was discarded. The volume of juice collected was 240 ml and its pH was 5.57.

With constant stirring, the pH was slowly adjusted downward with dilute phosphoric acid ($H_3PO_4$). A juice sample (35 ml) was removed at each of the following pH values: pH 5.4, pH 5.3, pH 5.2, pH 5.1, and pH 5.0. Subsequently, all samples were heated to 45° C. in a water bath and maintained at this temperature for ten minutes. Samples were then cooled to 25° C. in a cold water bath. The cooled samples were centrifuged at 10,000×G for 15 minutes.

The supernatants (S1 in FIG. 1) were decanted and analyzed for Fraction 1 protein level by the Bradford assay and SDS-PAGE. The virus was PEG-precipitated and isolated from a portion of each supernatant (25 ml) by the method of Gooding, supra. Virus concentrations were determined by spectrophotometric analysis at 260 nm.

TABLE 1

Total protein concentrations and virus yields in S1 portion after green juices are adjusted to low pH and heated at 45° C. for 10 minutes.

| pH of Green Juice | Total Protein Concentration in S1 (mg/ml) | Virus Yield (mg/g of fresh weight) |
| --- | --- | --- |
| 5.4 | 4.44 | 0.22 |
| 5.3 | 3.77 | 0.21 |
| 5.2 | 2.30 | 0.22 |
| 5.1 | 1.41 | 0.23 |
| 5.0 | 0.88 | 0.20 |

Results

The total protein as determined by the method of Bradford retained in the soluble portion (S1) was determined by the method of Bradford after centrifugation is gradually reduced when the pH of the green juice is adjusted downwards from 5.4 to 5.0. In particular, at pH 5.0 of green juice followed by heat-treatment at 45° C. for 10 minutes (referred to as "pH 5.0/45° C. process"), the amount of Fraction 1 protein left in S1 shows more than a five-fold reduction compared to the pH 5.5/45° C. process. More Fraction 1 protein is pelleted at low pH value of green juice. The insolubility of virus in S1, however, remains unaffected.

Subsequent examples also demonstrate that while Fraction 1 protein is pelleted at this pH range, the majority of Fraction 2 proteins remains in the supernatant. A conventional method of isolating soluble plant proteins adjusts the pH of green juice within the range of 5.3–6.0, which directs Fraction 1 protein to the supernatant after the centrifugation. The pH adjustment of green juice to a value below 5.2 followed by moderate heating in the instant procedure thus allows the separation of Fraction 1 and Fraction 2 protein upon the centrifugation of green juice. Eliminating the abundant Fraction 1 protein from the soluble portion simplifies the subsequent isolation and purification of Fraction 2 proteins. An ultrafiltration method can now be successfully applied to the purification of Fraction 2 proteins. This is an appreciable advantage over the prior art, where Fraction 1 protein is preferably retained in the soluble portion until the final crystallization or precipitation. Ultrafiltration in the presence of a large amount of Fraction 1 protein and other host materials is not efficient.

Example 2

Distribution of Virus From Green Juice at Different pH Values

Nicotiana tabacum (KY8959) grown in a greenhouse was inoculated with a TMV derivative (coat protein loop fusion), TMV291, seven weeks post seed germination. Plants were harvested two and half weeks post inoculation after systemic spread of the virus. Leaf and stalk tissue (150 g) was macerated in a 1-liter Waring blender for two minutes at the high setting with 0.04% $Na_2S_2O_5$ (150 ml). The macerated material was strained through four layers of cheesecloth to remove fibrous material. The remaining green juice was adjusted to the pHs of 5.0, 4.8, 4.6, 4.4, 4.2, and 4.0 with $H_3PO_4$. Green juice aliquots of 30 ml were removed at each pH for further processing. All pH adjusted green juice samples were heat-treated at 45° C. for 15 minutes in a water bath and then cooled to 15° C. Samples were centrifuged in a JS-13.1 rotor at 10,000 RPM for 15 minutes resulting in two fractions, supernatant (S1) and pellet (P1) (see FIG. 1). Pellets were resuspended in 15 ml of 50 mM phosphate buffer, pH 7.2 and centrifuged in a JS-13.1 rotor at 10,000 RPM for 15 minutes resulting in two fractions, supernatants (S2) and pellet (P2), see FIG. 1. Virus was recovered from both supernatant fractions by PEG-precipitation (8,000 MW PEG) as described by Gooding, supra and quantified by spectrophotometric analysis at 260 nm.

TABLE 2

Distribution of Virus in S1 and S2 at Different Green Juice pHs

| pH of Green Juice | Supernatant | Virus (mg) | Ratio of Virus (S2/S1) |
|---|---|---|---|
| 5.00 | S1 | 0.400 | |
| 5.00 | S2 | 0.482 | 1.21 |
| 4.80 | S1 | 0.200 | |
| 4.80 | S2 | 0.570 | 2.85 |
| 4.60 | S1 | 0.107 | |
| 4.60 | S2 | 0.486 | 4.54 |
| 4.40 | S1 | 0.016 | |
| 4.40 | S2 | 0.696 | 43.5 |
| 4.20 | S1 | 0.010 | |
| 4.20 | S2 | 0.859 | 85.9 |
| 4.00 | S1 | 0.006 | |
| 4.00 | S2 | 0.799 | 133.2 |

Results

This example examines the relative distribution of virus in supernatant, S1 and S2, during the first and second centrifugation, respectively. S1 is obtained after pH adjustment of green juice, from 5.0 to 4.0, followed by heat treatment and centrifugation. The pellet (P1) is resuspended in a buffer (pH 7.2) and subsequently subjected to a second centrifugation, which produces supernatant (S2). The amount of virus recovered from S1 and S2 portion is similar at pH 5.0 of green juice in Table 2. Upon lowering the pH, however virus gradually migrates from the supernatant portion (S1) to the pellet portion (P1) and reappears in S2. At pH 4.0 in Table 2, the amount of virus isolated from S2 portion is more than 100-fold higher than in the S1 portion. The pH of green juice and the pH of the resuspension buffer are shown to have a great effect on the relative distribution of virus in the supernatant or pellet during centrifugation. At a low pH, e.g. pH 4.0/45° C. process and pH 7.2 suspension buffer, the virus can be quantitatively recovered from the S2 portion alone. This process concentrates the virus into one fraction. This results in a fraction that can be ultrafiltered thereby significantly reducing the process volume and overall efficiency of virus purification. Adjusting the pH value of the green juice and suspension buffer offers a method for controlling the distribution of virus and thus facilitates the isolation of virus with large recovery yields.

Example 3
Small-Scale Isolation of Virus From S2 Using the pH 4.2/45° C. Process A tobacco plant of variety MD609 was inoculated with TMV 811. Eleven weeks after sowing, the plant was harvested. Leaf and stalk tissue (250 g) were combined with 0.04% sodium metabisulfite solution (250 ml) in a 1-liter Waring blender. The plant tissue was ground on high speed for a period of two minutes. The resulting homogenate was pressed through four layers of cheesecloth and the pressed fiber discarded. The volume of juice collected was 408 ml and its pH was 5.4. With constant stirring, the pH was adjusted to 4.2 with dilute phosphoric acid.

A portion of the juice (285 ml) was heated to 45° C. in a water bath and maintained at this temperature for 10 minutes. Without cooling, the juice was centrifugated at 10,000×G for 15 minutes. The supernatant was decanted and discarded, and the pellet was resuspended in double distilled deioninzed water (142 ml). The pH of the resuspended pellet was adjusted to pH 8.0 with dilute sodium hydroxide.

The resuspended and pH-adjusted pellet was divided into eight aliquots (15 ml each. These aliquots were centrifuged at different RPMs in a JA-20 rotor in a Beckman J2-21 centrifuge. The second supernatants (S2) were decanted and analyzed by SDS-PAGE. The virus was PEG-precipitated and isolated from the remaining supernatant (S2) portion according to the method of Gooding, supra. Supernatant clarity was also gauged visually.

TABLE 3

Virus and Protein Yields of S2 under Different Centrifugation Conditions.

| Aliquots | RPM | Minutes | Protein Conc. (mg/ml) | Virus Yield (mg/g fresh weight) | Appearance |
|---|---|---|---|---|---|
| 1 | 11,500 | 15 | 0.82 | 0.349 | Clear |
| 2 | 1,500 | 1 | 2.54 | Not Determined | Cloudy green |
| 3 | 1,500 | 3 | 2.12 | Not Determined | Cloudy green |
| 4 | 3,000 | 1 | 1.74 | Not Determined | Cloudy green |
| 5 | 3,000 | 3 | 1.25 | Not Determined | Slightly cloudy |
| 6 | 6,000 | 1 | 1.00 | 0.364 | Slightly cloudy |
| 7 | 6,000 | 3 | 0.93 | 0.359 | Almost clear |
| 8 | 9,000 | 3 | 0.85 | 0.348 | Almost clear |

Results

Example 2 demonstrates that a low pH of green juice and a neutral pH of suspension buffer directs most of virus into the soluble portion of the second centrifugation (S2). Example 3 further tests the optimal condition for the second centrifugation. If the target species is a virus, one prefers that the supernatant S2 contains as little protein as possible. Such a condition can be generally achieved with a high speed centrifugation for a long time interval, as shown in Aliquot 1 in Table 3. Such a condition, although effective, confers a larger cost and a longer process. An optimal condition provides a lower RPM rate for a shorter period of time without greatly compromising the yield and purity is desirable. Although Aliquots 2–5 operate at a much lower centrifugation speed and for a shorter period, the exclusion of protein is, however, poor, as evidenced by a larger soluble protein concentration and a cloudy solution (an indication of large protein content). Aliquots 6–8 leave much protein out of supernatant (an almost clear solution), the amount of virus recovered in the S2 portion is comparable to that of Aliquot 1, but confers only moderate centrifugation speed and shorter time interval comparing to aliquot 1.

Although it can be seen from the instant example that there is no danger of over centrifuging (Aliquot 1), for a cost-effect virus purification process, centrifugation at a moderate speed and reasonable time interval, sufficient to eliminate the interfering proteins, is preferred. Those skilled in the art can readily determine the optimal condition of centrifugation that is suitable for isolation of virus of interest.

Example 4
Effect of Host Components an Suspension Volume on Virus Recovery From S2 Using the pH 4.2/45° C. Process Nicotiana tabacum MD609 grown in a greenhouse was inoculated with a TMV derivative (coat protein leaky-stop), TMV811, six weeks post seed germination. Plants were harvested five weeks post inoculation after systemic spread of the virus. Leaf and stalk tissue (150 g) was macerated in a 1-liter Waring blender for two minutes at the high setting with 0.04% $Na_2S_2O_5$ (150 ml). The macerated material was strained through four layers of cheesecloth to remove fibrous material. The remaining green juice was adjusted to a pH of 4.2 with $H_3PO_4$. The pH-adjusted green juice was heated to 45° C. under hot tap water and incubated for 10 minutes in a 45° C. water bath. The heat-treated green juice was separated into 30 ml aliquots and then centrifuged in a JS-13.1 rotor at 10,000 RPM for 15 minutes. The pelleted material was adjusted to either 10 or 20% of the starting 30 ml volume by the addition of supernatant and then further adjusted to ¼, ½ or 1 volume of the starting 30 ml volume by the addition of deionized $H_2O$. The average pellet volume from 30 ml of green juice was 1.7 ml.

All pellets were completely resuspended in the added supernatant and deionized $H_2O$ and then adjusted to a pH of 7.5–7.7 by the addition of NaOH. The resuspended samples were centrifuged in a JS13.1 rotor at 10,000 RPM for 15 minutes. Virus was recovered from the supernatants by PEG-precipitation (8,000 MW PEG) as described by Gooding, supra.

Table 4 demonstrates the inverse relationship of resuspension volume to virus yield. When resuspension volume increases from ¼ and ½ to 1 equivalent of the starting volume (30 ml), the recovery of virus is increased (compare 1 through 3 and 4 through 6). Thus, as the percentage of pellet volume increases, the resuspension volume should also increase to maximize the recovery of virus. For the effect of residual supernatant, the yield of virus recovery is higher when less supernatant is added back to the pellet (compare 1 and 4, 2 and 5, 3 and 6). Host component(s) in the supernatant may affect the ability to resuspend/dissociate virions from the pellet. Thus, a smaller pellet volume with less residual supernatant after centrifugation is desirable. In summary, factors such as the resuspension volume and dryness of the pellet may be optimized to maximize the yield and purify of target species.

Example 5
Effect of Feed Rate on Large Scale Virus Isolation Using pH 5.0/47° C. Process Field grown tobacco of variety KY8959 was inoculated with TMV 291 and harvested ten weeks after setting. The plant tissue (8.093 lbs.) was ground in a Reitz® disintegrator and the fiber removed using a screw press. Water was added to the disintegrator at the rate of 120 gallons per ton of tobacco. The juice from the press was collected in a stirred tank where the pH was adjusted to 5.0 with phosphoric acid. The pH-adjusted juice was pumped through a heat exchanger in a continuous manner so that the temperature of the juice reached 47° C. The heated juice was then pumped through holding tubes, which ensures that this temperature was maintained for at least ten minutes.

The treated juice was then fed to a Westfalia® SAMR 15037 disk stack-type centrifuge at a feed rate of five gallons per minute to twenty gallons per minute. Samples of the concentrate were taken at each feed rate and analyzed for virus concentration.

TABLE 4

Virus Yield under Different Resuspension Volume.

| Pellet | Pellet Volume (ml) | Supernatant added back (ml) | (Added Supernatant + Pellet)/Initial Volume | deionized $H_2O$ added (ml) | Total Resuspension Volume in ml (ratio) | Virus mg/g fresh weight extracted |
|---|---|---|---|---|---|---|
| 1 | 1.7 | 1.3 | 10% | 4.5 | 7.5 (¼) | 0.798 |
| 2 | 1.7 | 1.3 | 10% | 12.0 | 15.0 (½) | 0.877 |
| 3 | 1.7 | 1.3 | 10% | 27.0 | 30.0 (1) | 0.985 |
| 4 | 1.7 | 4.3 | 20% | 1.5 | 7.5 (¼) | 0.489 |
| 5 | 1.7 | 4.3 | 20% | 9.0 | 15.0 (½) | 0.836 |
| 6 | 1.7 | 4.3 | 20% | 24.0 | 30.0 (1) | 0.952 |

Results

When pellets are obtained from centrifugation, there are frequently contaminated with residual supernatant, which may or may not affect the subsequent recovery of the target species. In addition, the resuspension volume may also exert an effect on the recovery of target species. This example is designed to test the virus recovery under the condition where a defined volume of supernatant is added back to the pellet and the resuspension volume is systematically varied in order to assess its effect on virus recovery.

TABLE 5

Virus Yield Versus Feed Rate.

| Sample | Feed Rate (GPM) | Virus Conc. (mg/ml) |
|---|---|---|
| 1 | 5 | 2.05 |
| 2 | 10 | 3.40 |

TABLE 5-continued

Virus Yield Versus Feed Rate.

| Sample | Feed Rate (GPM) | Virus Conc. (mg/ml) |
|---|---|---|
| 3 | 15 | 4.03 |
| 4 | 20 | 4.23 |

Results

The virus recovery yield was examined using different feed rates. Table 5 shows that virus recovery was lowered wit a low feed rate of green juice to the centrifuge. Since the feed rate is inversely proportional to the retention time of green juice in the centrifuge, these data demonstrate virus is lost if it is subjected to too much centrifugation (low feed rate). Thus, feed rate may also be optimized to maximize the yield and purity of target species in a large scale isolation and purification.

Example 6
Isolation of Recombinant Protein α-Trichosanthin Using the pH 5.0/45° C. Process

*Nicotiana benthamiana* grown in a greenhouse was inoculated with TMV containing the gene coding for α-trichosanthin. Plants were harvested ten days post inoculation after systemic spread of the virus. Leaf and stalk tissue (150 g) was macerated in a 1-liter Waring blender for two minutes at the high setting with 0.4% $Na_2S_2O_5$ (150 ml). The macerated material was strained through four layers of cheesecloth to remove fibrous material. The remaining green juice was adjusted to pH 5.0 with HCl. The pH adjusted green juice was heat-treated at 45° C. for ten minutes in a water bath and then cooled to 28° C. Heat treated juice was centrifuged in a KA-12 rotor (Kompspin, Sunnyvale, Calif.) at 10,000 RPM (15,600×G) for 15 minutes. The supernatant (S1) (50 ml aliquots) was subjected to ultrafiltration using 100 and 10 kD MWCO regenerated cellulose membranes in an Amicon® stirred-cell at 50 PSI. The 100 kD permeate fraction was then concentrated via filtration through a 10 kD membrane and diafiltered three times. The α-trichosanthin is collected from the 10 kD concentrate. The 10 kD permeate contains the sugars, alkaloids, flavors, vitamins and peptides below 10 kD MW. The relative quantity of α-trichosanthin in green juice, supernatant, 100 kD and 10 kD concentrates and the 100 to 10 kD fraction was determined by Western analysis using α-trichlosanthin antibody.

TABLE 6

α-trichosanthin Yield in a pH 5.0/45° C. process.

| Fraction | Mg Total Protein as Determined by Bradford Analysis | Percentage of α-trichosanthin Recovered Relative to Green Juice Based Upon Western Analysis |
|---|---|---|
| Green juice | 134 | 100 |
| S1 | 22 | 100 |
| 100 kD Concentrate | 28.5 | 96 |
| 100 kD Concentrate | 16.3 | 40.8 |
| 10 kD Permeate | 5.7 | Not Determined |
| 100–10 kD Fraction | 5.4 | 34 |

Results

This example demonstrates the ability to extract and purify a soluble F2 protein, α-trichosanthin, using the pH 5.0/45° C. process and ultrafiltration. The α-trichlosanthin was quantitatively retained in the supernatant (S1) fraction, relative to amounts present in the green juice, (based upon Western analysis). In addition, α-trichosanthin present in the S1 was purified 6-fold relative to green juice (based on Bradford protein and Western analysis).

α-Trichosanthin present in the S1 fraction was quantitatively retained and concentrated 4-fold, by ultrafiltration using a 10 kD MWCO membrane (50 ml of S1 was concentrated to 13.5 ml and 96% of the α-trichlosanthin was present in the 10 kD concentrate, based upon Western analysis.

αTrichlosanthin was also purified away from large molecular weight proteins and viruses via ultrafiltration with a 100 kD MWCO membrane. The 100 kD concentrate fraction was diafiltered three times to allow recovery of additional α-Trichosanthin. After 100 kD concentration and diafiltration, only 40.8% of the α-Trichosanthin remained in the 100 kD concentrate, indicating that 59.2% of the α-Trichosanthin would be present in the 100 kD permeate fraction. The 100 kD permeate fraction was concentrated using a 10 kD MWCO membrane. The resultant 10 kD concentrate (derived from the 100 kD permeate), contained 34% of α-Trichosanthin, relative to the amount of αTrichosanthin present in 50 ml of the starting S1 fraction. The α-trichosanthin present in the 100-10 kD fraction was determined to be purified 8-fold relative to Green juice (based on Bradford protein and Western analysis) and concentrated 12.5-fold (50 ml of S1 was concentrated to 4.0 ml of 100-10 kD fraction).

EXAMPLE 7
Isolation of Secretory IgA Antibody from Transgenic Plants using the pH5.0/47° C. Process Leaf and stalk tissue (50 g fresh weight) of greenhouse grown transgenic tobacco, which expresses four secretory IgA (SIgA) protein components, was macerated in a Virtis blender for two minutes at the high setting with 0.04% $Na_2S_2O_5$ (75 ml). The macerated material was strained through four layers of cheesecloth to remove fibrous material. The remaining green juice was adjusted to pH 5.0 with $H_3PO_4$. The pH-adjusted green juice was heat-treated at 47° C. for ten minutes in a water bath and then cooled to 28° C. Heat treated juice was centrifuged in a JA-13.1 rotor at 3,000 RPM for three minutes. The supernatant fraction was subjected to ultrafiltration using 10 kD MWCO, regenerated cellulose membrane (Amicon®, Centriprep®). The relative quantity of SIgA in green juice, supernatant and the 10 kD concentrate was determined by Western analysis using an antibody reactive with the heavy chain.

TABLE 7

Secretory IgA and Other Proteins Recovered from the pH 5.0/47° C. Process.

| Fraction | Mg Total Protein per ml (Bradford) | Percentage of Total Protein Relative to Green Juice | SIgA (ng/mg Fresh Weight) |
|---|---|---|---|
| Green juice | 1.78 | 100 | 100 |
| Supernatant (S1) | 0.25 | 14 | 30 |
| 10 kD Concentrate (12X) | 3.10 | 14 | 30 |

Results:

Secretory IgA antibody, recombinantly produced in transgenic plants, was successfully recovered in this example.

Following pH adjustment and heat treatment, centrifugation reduced the total protein in the supernatant by 85%. The SIgA in the supernatant was recovered and ultrafiltered resulting in a 12-fold concentration of the total protein and the SIgA components.

EXAMPLE 8

Small Scale Isolation of Virus using pH 5.0/45° C. Process and Ultrafiltration

Field-grown tobacco of variety MD609 and infected with TMV 261 was harvested and frozen at −20° C. until use. The frozen tissue was ground in four batches in a 4-liter Waring blender. In each batch, plant tissue (1500 g) was ground for three minutes at high speed in 0.04% sodium metabisulfite solution (1500 ml). The homogenates were strained through four layers of cheesecloth and the juices combined to give a volume of approximately 10 liters.

The pH of the juice was adjusted from a starting value of 5.8 to 5.0 using concentrated phosphoric acid ($H_3PO_4$). The juice was then heated to 45° C. using a stainless steel coil heated by hot tap water. After maintaining the juice at 45° C. for ten minutes, it was cooled to 25° C. using the coil with chilled water. The heat-treated juice was centrifuged at 12,000×G for five minutes and the resulting supernatant was decanted through Miracloth®.

This supernatant was processed using a one square foot, 100 kD MWCO regenerated cellulose, spiral ultrafiltration membrane. With an inlet pressure of 50 psi and a recirculation rate of five liters per minute, the supernatant was concentrated to about 5% of the starting volume. The final concentrate was drained from the ultrafiltration apparatus and the system was rinsed with a small volume of water. Samples of the starting supernatant, the final concentrate, the water rinse, and the combined permeate were assayed for protein by Bradford analysis. They were PEG-precipitated according to the method of Gooding, supra, to isolate any virus present. Virus concentrations were determined spectrophotometrically.

TABLE 8

Protein Concentration and Virus Yield in Supernatant (S1) and Subsequent Ultrafiltration.

| Sample | Total Protein (g) | Virus Yield (g) |
| --- | --- | --- |
| Supernatant | 3.35 | 1.94 |
| 100 kD MWCO Concentrate | 2.64 | 1.64 |
| 100 kD MWCO Permeate | 0.22 | Not Determined |
| Membrane Rinse | 0.38 | 0.40 |

Results:

In this example, a small scale virus isolation was successfully carried out. Green juice was pH adjusted to 5.0 and heat-treated followed by centrifugation. The supernatant containing virus (1.94 g) was passed through a 100 kD MWCO membrane. The virus (1.64 g) was quantitatively recovered from the concentrate. Proteins of smaller size were collected in the permeate. Only a small amount of virus is lost by ultrafiltration using a 100 kD membrane.

EXAMPLE 9

Large Scale Virus Isolation using pH 4.0/47° C. Process

Field grown tabacco of variety KY8959 was inoculated with TMV 291 and harvested ten weeks after setting. The plant tissue (8,382 lbs.) was ground in a Reitz® disintegrator and the fiber removed using a screw press. Water was added to the disintegrator at the rate of 120 gallons per ton of tobacco. The juice from the press was collected in a stirred tank where the pH was adjusted to 4.0 with phosphoric acid. The pH adjusted juice was pumped through a heat exchanger in a continuous manner so that the temperature of the juice reached 47° C. The heated juice was then pumped through holding tubes which ensures that this temperature was maintained for at least ten minutes.

The treated juice was then fed to a Westfalia SAMR 15037 disk stack type centrifuge at a feed rate of 10 gallons per minute. A total of 1120 gallons of supernatant and 200 gallons of pellet were produced during centrifugation. A volume of 380 gallons of water was added to the pellet, and the resuspended pellet pH was adjusted to 7.12 by the addition of KOH. The pH adjusted, resuspended pellet was then fed to a Westfalia SAMR 15037 disk stack type centrifuge at a feed rate of 5 gallons per minute resulting in the recovery of 435 gallons of supernatant (S2). Supernatant (435 gallons) was concentrated to 24.8 gallons by ultrafiltration through 1,000 square feet of 100 kD MWCO, cellulose acetate, spiral membrane (SETC, Livermore, Calif.). After removal of the concentrate, the membranes were washed with 31.5 gallons of water. Virus (158 g) was purified from the 100 kD MWCO concentrate and then further concentrated and washed by PEG-precipitation (8,000 MW PEG) as described by Gooding, supra. This quantity of virus recovered is two orders of magnitude greater than ever isolated before.

This example demonstrates an efficient large scale virus isolation using the pH4.0/47° C. process. Example 2, supra, demonstrates that the pH 4.0/47° C. process allows the concentration of virus in the supernatant, S2 on a small scale. The virus can be further concentrated using ultrafiltration by passing the supernatant (S2) through a 100 kD MWCO membrane. The virus particles can be recovered at high yield as shown in this example.

EXAMPLE 10

Large Scale Virus and Fraction 2 Protein Isolation using pH 5.0/47° C. Process

Field-grown tabacco of variety KY8959 was inoculated with TMV 291 and harvested ten weeks after setting. The plant tissue (8,093 lbs.) was ground in a Reitz® disintegrator and the fiber removed using a screw press. Water was added to the disintegrator at the rate of 120 gallons per ton of tobacco. The juice from the press was collected in a stirred tank where the pH was adjusted to 5.0 with phosphoric acid. The pH-adjusted juice was pumped through a heat exchanger in a continuous manner so that the temperature of the juice reached 47° C. The heated juice was then pumped through holding tubes which ensures that this temperature was maintained for at least 10 minutes.

The treated juice was then fed to a Westfalia® SAMR 15037 disk stack type centrifuge at a feed rate of ten gallons per minute. A total of 760 gallons of the 990 gallons of supernatant produced during centrifugation was concentrated to 32 gallons by ultrafiltration through 1,000 square feet of 100 kD MWCO, cellulose acetate, spiral membrane. Virus (213 g) was purified from the 100 kD concentrate fraction by PEG (8,000 MW) precipitation as described by Gooding, supra. The soluble Fraction 2 proteins (<100 kD) located in the 100-kD filtration permeate, were concentrated by ultrafiltration through 40 square feet of 10 kD MWCO, regenerated cellulose, spiral membrane. A total of 60 gallons of 100 kD permeate was concentrated to 3.5 gallons, yielding 1.69 g of soluble Fraction 2 proteins.

This example successfully demonstrates that a large-scale process for isolating and purifying Fraction 2 proteins and virus using pH 5.0/47° C. process. The first centrifugation produces a supernatant fraction that contains both virus and other soluable proteins. It is possible to use ultrafiltration to concentrate and separate the virus and soluble Fraction 2 proteins, where virus remains in the concentrate of a large MW MWCO membrane and Fraction 2 proteins in the permeate. Fraction 2 proteins can be further purified and concentrated by passing through a smaller MW MWCO membrane, where different sizes of Fraction 2 proteins can be individually obtained. Fraction 2 protein and virus can be recovered with high yields using the instant method at a large scale.

EXAMPLE 11

Physiochemical Properties of the Purified Virus Particles Produced by the pH5.0/47° C. or the pH4.0/47° C. Process Wild type tabacco mosaic virus (TMV204, sample 960808) was extracted from field grown tabacco (variety KY8959, 11,884 lbs.) using the large-scale pH4.0/47° C. process as described in Example 9. Recombinant TMV291 (sample 960829) was extracted from field grown tabacco (variety KY8959, 14,898 lbs.) using the pH5.0/47° C. extraction procedure as described in Example 10. The virion, after PEG precipitation, were subjected to various analyses to ascertain biochemical and purity profiles.

TABLE 9

Virion Purity Profiles after Large Scale Isolation using pH 4.0/47° C. and pH 5.0/47° C. Processes.

| Analysis | Sample 960808 (pH 4.0/47° C. process) | Sample 960829 (pH 5.0/47° C. process) |
|---|---|---|
| Absorbance ratio (260/280 nm) | 1.194 | 1.211 |
| *MALDI-TOF (molecular mass) | 17,507.3 | 18,512.5 |
| Moisture in percentage | 41.96 | 54.57 |
| Percentage of Total lipids (Wet weight basis) | 2.15 | 1.30 |

*Matrix Assisted Laser Desorption Ionization-Time of Flight, Mass Spectrometry.

TABLE 10

Elemental Analysis of Virions after Large Scale Isolation Using pH 4.0/47° C. and pH 5.0/47° C. Processes.

| Elemental Analysis (dry weight basis) | Sample 960808 (pH 4.0/47° C. process) | Sample 960829 (pH 5.0/47° C. process) |
|---|---|---|
| Carbon | 45.67% | 44.80% |
| Hydrogen | 6.58% | 6.48% |
| Nitrogen | 13.87% | 13.65% |
| Oxygen | 24.20% | 24.16% |
| Sulfur | 0.18% | <0.5% |
| Nicotine by HPLC | 1.44 ppm | 5.68 ppm |
| **Endotoxin EU/ml at 1.0 $\mu$g virus/ml | 0.2475 ± 0.13 | 0.1213 ± 0.03 |

**Endotoxin levels were determined by the Chromogenic Limulus Amebocyte Lysate Test.

TABLE 11

Amino Acid Analysis of Virions after Large Scale Isolation Using pH 4.0/47° C. and pH 5.0/47° C. Processes.

| ***Amino Acid Analysis $\mu$moles, reported on dry weight basis | Sample 960808 (pH 4.0/47° C. process) | Sample 960829 (pH 5.0/47° C. process) |
|---|---|---|
| Asp | 22.95 | 26.28 |
| Ser | 17.73 | 16.38 |
| Glu | 19.80 | 18.72 |
| Gly | 8.37 | 12.78 |
| Arg | 14.94 | 18.90 |
| Thr | 19.17 | 19.62 |
| Ala | 19.17 | 21.96 |
| Pro | 10.17 | 9.45 |
| Tyr | 4.68 | 4.14 |
| Val | 18.36 | 18.63 |
| Lys | 1.71 | 2.43 |
| Ile | 9.81 | 10.26 |
| Leu | 15.30 | 15.39 |
| Phe | 10.18 | 10.08 |

***Quantity of sample analyzed, wet weight (960808: 537.47 mg, 960829: 554.28 mg).
***Quantity of sample analyzed, wet weight (960808: 537.47 mg, 960829: 554.28 mg).

Results:

The analysis of PEG purified virion preparations produced via the large-scale pH5.0/47° C. and pH4.0/47° C. processes, indicate a high degree of purity and no detectable TMV coat protein degradation. Absorbance ratios of 1.20 at 260/280 nm (Table 9) are indicative of highly purified TMV. In addition, the MALDI-TOF mass of both virus preparations (Table 9) are within experimental ranges for the predicted coat protein molecular weight. Both virus preparations contained low levels of lipids, nicotine and endotoxin, again demonstrating the utility of these methods in the isolation and purification of virions and virus fusion coat protein. The elemental analyses of the virus extracts (Table 10) are indicative of highly purified proteins as determined by the relative ratios of the various elements. The amino acid profiles of the virus samples (Table 11) reflect the relative abundance of each predicated amino acid and also reflects the predicted differences in amino acids between the two test samples.

Both virus samples were shown to be infective when passed onto host plants, indicating that the described methods resulted in the recovery of biologically active virions. RT-PCR analysis of the virus extracts produced the predicated nucleic acid fragments, indicative of intact RNA genomes.

Although the invention has been described with reference to the presently preferred embodiments, it should be understood that various modifications can be made without departing from the spirit of the invention. Accordingly, the invention is limited only by the following claims.

We claim:

1. A method for obtaining a soluble protein or peptide from a plant comprising the sequential steps of:
    (a) homogenizing a plant to produce a green juice homogenate;
    (b) adjusting the pH of the green juice homogenate to less than or equal to about 5.2;
    (c) heating the green juice homogenate to a minimum temperature of about 45° C.;
    (d) centrifuging the green juice homogenate to produce a supernatant; and
    (e) purifying the protein or peptide from the supernatant.

2. The method of claim 1 wherein the pH of the green juice homogenate is adjusted to between about 4.0 and 5.2.

3. The method of claim 1 wherein the pH of the green juice homogenate is adjusted to about 5.0.

4. The method of claim 1 wherein the green juice homogenate is heated to a temperature of between about 45 and 50° C.

5. The method according to claim 1 wherein the supernatant produced in step (d) is further subjected to ultrafiltration.

6. The method according to claim 5 further comprising the step of subjecting a permeate produced by the said ultrafiltration to a second ultrafiltration.

7. The method according to claim 6 further comprising the step of purifying a concentrate resulting from the second ultrafiltration.

8. The method of claim 7 wherein said purifying is performed by chromatography, affinity-based method of purification, or salt precipitation.

9. The method of any one of claim 1 through 8 wherein the soluble protein or peptide is selected from the group consisting of IL-1, IL-2, IL-3, IL-4, Il-5, IL-6, IL-7, Il-8, IL-9, IL-10, IL-11, IL-12, EPO, G-CSF, GM-CSF, M-CSF, Factor VIII, Factor IX, tPA, receptors, receptor antagonists, antibodies, single-chain antibodies, enzymes, neuropolypeptides, insulin, antigens, vaccines, peptide hormones, calcitonin, and human growth hormone.

10. The method of any one of claims 1 through 8 wherein the soluble protein or peptide is an antimicrobial peptide or protein and is selected from the group consisting of protegrins, magainins, cecropins, melittins, indolicidins, defensions, β-defensins, cryptdins, clavainins, plant defensins, nicin and bactenecins.

11. The method of any one of claims 1 through 8 wherein the said protein or peptide is a recombinant protein or peptide.

12. The method according to claim 5 wherein said ultrafiltration produces a permeate comprising one or more molecules selected from the group consisting of sugars, polysaccharides, vitamins, alkaloids, flavor compounds and peptides.

13. The method according to claim 7 wherein said second ultrafiltration produces a permeate containing molecules selected from the group consisting of sugars, polysaccharides, vitamins, alkaloids, flavor compounds and peptides.

14. The method according to any one of the claims 1–8 wherein said protein or peptide is non-native in the plant.

15. A method for obtaining a fusion peptide or fusion protein from a plant comprising the sequential steps of:
    (a) homogenizing a plant to produce a green juice homogenate;
    (b) adjusting the pH of the green juice homogenate to less than or equal to about 5.2;
    (c) heating the green juice homogenate to a minimum temperature of about 45° C.;
    (d) centrifuging the green juice homogenate to produce a pellet;
    (e) resuspending the pellet in a liquid solution;
    (f) adjusting the pH of the liquid solution containing the resuspended pellet to about 2.0 to 4.0;
    (g) centrifuging the liquid solution of step (f) containing the resuspended pellet to about 2.0 to 4.0;
    (h) purifying the fusion protein or fusion peptide.

16. The method according to claim 15 wherein the purifying is performed by at least one method selected from the group consisting of chromatography, ultrafiltration, and salt precipitation.

17. The method of claim 15 or claim 16 wherein said fusion protein or fusion peptide comprises a peptide or protein selected from the group consisting of IL-1, IL-2, IL-3, IL-4, Il-5, IL-6, IL-7, Il-8, IL-9, IL-10, IL-11, IL-12, EPO, G-CSF, GM-CSF, hPG-CSF, M-CSF, Factor VIII, Factor IX, tPA, hGH, receptors, receptor antagonists, antibodies, single-chain antibodies, enzymes, neuropolypeptides, insulin, antigens, vaccines, and calcitonin.

18. The method of claim 15 or claim 16 wherein said fusion protein or fusion peptide comprises an antimicrobial peptide or antimicrobial protein selected from the group consisting of protegrins, magainins, cecropins, melittins, indolicidins, defensins, β-defensins, cryptdins, clavainins, plant defensins, nicin and bactenecins.

19. A method for obtaining a soluble protein or peptide from a plant comprising the sequential steps of:
    (a) harvesting a plant;
    (b) homogenizing the plant to produce a green juice homogenate;
    (c) adjusting the pH of the green juice homogenate to less than or equal to about 5.2.
    (d) heating the green juice homogenate to a minimum temperature of about 45° C.;
    (e) centrifuging the green juice homogenate to produce a supernatant; and
    (f) purifying the protein or peptide from the supernatant.

20. A method for obtaining a soluble protein or peptide from a plant comprising the sequential steps of:
    (a) inserting a virus into a plant;
    (b) harvesting the plant;
    (c) homogenizing the plant to produce a green juice homogenate;
    (d) adjusting the pH of the green juice homogenate to less than or equal to about 2.5.
    (e) heating the green juice homogenate to a minimum temperature of about 45° C.
    (f) centrifuging the green juice homogenate to produce a supernatant; and
    (g) purifying the protein or peptide from the supernatant.

21. The method according to claim 20 wherein the virus is a recombinant virus.

22. The method according to claim 21 wherein the virus is a viral vector capable of carrying a heterologous nucleic acid sequence.

23. The method according to any one of the claims 19–22 wherein said protein or peptide is non-native in the plant.

24. The method according to any one of the claims 19–22 wherein said protein or peptide is a recombinant protein or peptide.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 6395 base pairs
        (B) TYPE: nucleic acid
        (C) STRANDEDNESS: single
        (D) TOPOLOGY: unknown (ii) MOLECULE TYPE: Genomic RNA (xi) SEQUENCE DESCRIPTION: SEQ ID NO:1:

```
GUAUUUUUAC AACAAUUACC AACAACAACA AACAACAAAC AACAUUACAA UUACUAUUUA      60

CAAUUACAAU GGCAUACACA CAGACAGCUA CCACAUCAGC UUUGCUGGAC ACUGUCCGAG     120

GAAACAACUC CUUGGUCAAU GAUCUAGCAA AGCGUCGUCU UUACGACACA GCGGUUGAAG     180

AGUUUAACGC UCGUGACCGC AGGCCCAAGG UGAACUUUUC AAAAGUAAUA AGCGAGGAGC     240

AGACGCUUAU UGCUACCCGG GCGUAUCCAG AAUUCCAAAU UACAUUUUAU AACACGCAAA     300

AUGCCGUGCA UUCGCUUGCA GGUGGAUUGC GAUCUUUAGA ACUGGAAUAU CUGAUGAUGC     360

AAAUUCCCUA CGGAUCAUUG ACUAUGACA UAGGCGGGAA UUUUGCAUCG CAUCUGUUCA      420

AGGGACGAGC AUAUGUACAC UGCUGCAUGC CCAACCUGGA CGUUCGAGAC AUCAUGCGGC     480

ACGAAGGCCA GAAAGACAGU AUUGAACUAU ACCUUUCUAG GCUAGAGAGA GGGGGGAAAA     540

CAGUCCCCAA CUUCCAAAAG GAAGCAUUUG ACAGAUACGC AGAAAUUCCU GAAGACGCUG     600

UCUGUCACAA UACUUUCCAG ACAAUGCGAC AUCAGCCGAU GCAGCAAUCA GGCAGAGUGU     660

AUGCCAUUGC GCUACACAGC AUAUAUGACA UACCAGCCGA UGAGUUCGGG GCGGCACUCU     720

UGAGGAAAAA UGUCCAUACG UGCUAUGCCG CUUUCCACUU CUCCGAGAAC CUGCUUCUUG     780

AAGAUUCAUA CGUCAAUUUG GACGAAAUCA ACGCGUGUUU UUCGCGCGAU GGAGACAAGU     840

UGACCUUUUC UUUUGCAUCA GAGAGUACUC UUAAUUAUUG UCAUAGUUAU UCUAAUAUUC     900

UUAAGUAUGU GUGCAAAACU UACUUCCCGG CCUCUAAUAG AGAGGUUUAC AUGAAGGAGU     960

UUUUAGUCAC CAGAGUUAAU ACCUGGUUUU GUAAGUUUUC UAGAAUAGAU ACUUUUCUUU    1020

UGUACAAAGG UGUGGCCCAU AAAAGUGUAG AUAGUGAGCA GUUUAUACU GCAAUGGAAG     1080

ACGCAUGGCA UUACAAAAAG ACUCUUGCAA UGUGCAACAG CGAGAGAAUC CUCCUUGAGG    1140

AUUCAUCAUC AGUCAAUUAC UGGUUUCCCA AAAUGAGGGA UAUGGUCAUC GUACCAUUAU    1200

UCGACAUUUC UUUUGGAGACU AGUAAGAGGA CGCGCAAGGA AGUCUUAGUG UCCAAGGAUU    1260

UCGUGUUUAC AGUGCUUAAC CACAUUCGAA CAUACCAGGC GAAAGCUCUU ACAUACGCAA    1320

AUGUUUUGUC CCUUGUCGAA UCGAUUCGAU CGAGGGUAAU CAUUAACGGU GUGACAGCGA    1380

GGUCCGAAUG GGAUGUGGAC AAAUCUUUGU UACAAUCCUU GUCCAUGACG UUUUACCUGC    1440

AUACUAAGCU UGCCGUUCUA AAGGAUGACU UACUGAUUAG CAAGUUUAGU CUCGGUUCGA    1500

AAACGGUGUG CCAGCAUGUG UGGGAUGAGA UUUCGCUGGC GUUUGGGAAC GCAUUUCCCU    1560

CCGUGAAAGA GAGACUCUUG AACAGGAAAC UUAUCAGAGU GGCAGGCGAC GCAUUAGAGA    1620

UCAGGGUGCC UGAUCUAUAU GUGACCUUCC ACGACAGAUU AGUGACGAG UACAAGGCCU     1680

CUGUGGACAU GCCUGCGCUU GACAUUAGGA GAAGAUGGA AGAAACGGAA GUGAUGUACA     1740

AUGCACUUUC AGAGUUAUCG GUGUUAAGGG AGUCUGACAA AUUCGAUGUU GAUGUUUUUU    1800
```

```
CCCAGAUGUG CCAAUCUUUG GAAGUUGACC CAAUGACGGC AGCGAAGGUU AUAGUCGCGG   1860

UCAUGAGCAA UGAGAGCGGU CUGACUCUCA CAUUUGAACG ACCUACUGAG GCGAAUGUUG   1920

CGCUAGCUUU ACAGGAUCAA GAGAAGGCUU CAGAAGGUGC AUUGGUAGUU ACCUCAAGAG   1980

AAGUUGAAGA ACCGUCCAUG AAGGGUUCGA UGGCCAGAGG AGAGUUACAA UUAGCUGGUC   2040

UUGCUGGAGA UCAUCCGGAG UCGUCCUAUU CUAAGAACGA GGAGAUAGAG UCUUUAGAGC   2100

AGUUUCAUAU GGCGACGGCA GAUUCGUUAA UUCGUAAGCA GAUGAGCUCG AUUGUGUACA   2160

CGGGUCCGAU UAAAGUUCAG CAAAUGAAAA ACUUUAUCGA UAGCCUGGUA GCAUCACUAU   2220

CUGCUGCGGU GUCGAAUCUC GUCAAGAUCC UCAAAGAUAC AGCUGCUAUU GACCUUGAAA   2280

CCCGUCAAAA GUUUGGAGUC UUGGAUGUUG CAUCUAGGAA GUGGUUAAUC AAACCAACGG   2340

CCAAGAGUCA UGCAUGGGGU GUUGUUGAAA CCCACGCGAG GAAGUAUCAU GUGGCGCUUU   2400

UGGAAUAUGA UGAGCAGGGU GUGGUGACAU GCGAUGAUUG GAGAAGAGUA GCUGUUAGCU   2460

CUGAGUCUGU UGUUUAUUCC GACAUGGCGA AACUCAGAAC UCUGCGCAGA CUGCUUCGAA   2520

ACGGAGAACC GCAUGUCAGU AGCGCAAAGG UUGUUCUUGU GGACGGAGUU CCGGGCUGUG   2580

GAAAAACCAA AGAAAUUCUU UCCAGGGUUA AUUUGAUGA AGAUCUAAUU UUAGUACCUG   2640

GGAAGCAAGC CGCGGAAAUG AUCAGAAGAC GUGCGAAUUC CUCAGGGAUU AUUGUGGCCA   2700

CGAAGGACAA CGUUAAAACC GUUGAUUCUU UCAUGAUGAA UUUUGGGAAA AGCACACGCU   2760

GUCAGUUCAA GAGGUUAUUC AUUGAUGAAG GGUUGAUGUU GCAUACUGGU UGUGUUAAUU   2820

UUCUUGUGGC GAUGUCAUUG UGCGAAAUUG CAUAUGUUUA CGGAGACACA CAGCAGAUUC   2880

CAUACAUCAA UAGAGUUUCA GGAUUCCCGU ACCCCGCCCA UUUUGCCAAA UUGGAAGUUG   2940

ACGAGGUGGA GACACGCAGA ACUACUCUCC GUUGUCCAGC CGAUGUCACA CAUUAUCUGA   3000

ACAGGAGAUA UGAGGGCUUU GUCAUGAGCA CUUCUUCGGU UAAAAAGUCU GUUUCGCAGG   3060

AGAUGGUCGG CGGAGCCGCC GUGAUCAAUC CGAUCUCAAA ACCCUUGCAU GGCAAGAUCC   3120

UGACUUUUAC CCAAUCGGAU AAAGAAGCUC UGCUUUCAAG AGGGUAUUCA GAUGUUCACA   3180

CUGUGCAUGA AGUGCAAGGC GAGACAUACU CUGAUGUUUC ACUAGUUAGG UUAACCCCUA   3240

CACCAGUCUC CAUCAUUGCA GGAGACAGCC CACAUGUUUU GGUCGCAUUG UCAAGGCACA   3300

CCUGUUCGCU CAAGUACUAC ACUGUUGUUA UGGAUCCUUU AGUUAGUAUC AUUAGAGAUC   3360

UAGAGAAACU UAGCUCGUAC UUGUUAGAUA UGUAUAAGGU CGAUGCAGGA ACACAAUAGC   3420

AAUUACAGAU UGACUCGGUG UUCAAGGGUU CCAAUCUUUU UGUUGCAGCG CCAAAGACUG   3480

GUGAUAUUUC UGAUAUGCAG UUUUACUAUG AUAAGUGUCU CCCAGGCAAC AGCACCAUGA   3540

UGAAUAAUUU UGAUGCUGUU ACCAUGAGGU UGACUGACAU UUCAUUGAAU GUCAAAGAUU   3600

GCAUAUUGGA UAUGUCUAAG UCUGUUCGUG CGCCUAAGGA UCAAAUCAAA CCACUAAUAC   3660

CUAUGGUACG AACGGCGGCA GAAAUGCCAC GCCAGACUGG ACUAUUGGAA AAUUUAGUGG   3720

CGAUGAUUAA AAGAAACUUU AACGCACCCG AGUUGUCUGG CAUCAUUGAU AUUGAAAAUA   3780

CUGCAUCUUU GGUUGUAGAU AAGUUUUUUG AUAGUUAUUU GCUUAAAGAA AAAAGAAAAC   3840

CAAAUAAAAA UGUUUCUUUG UUCAGUAGAG AGUCUCUCAA UAGAUGGUUA GAAAAGCAGG   3900

AACAGGUAAC AAUAGGCCAG CUCGCAGAUU UUGAUUUUGU GGAUUUGCCA GCAGUUGAUC   3960

AGUACAGACA CAUGAUUAAA GCACAACCCA AACAAAGUU GGACACUUCA AUCCAAACGG   4020

AGUACCCGGC UUUGCAGACG AUUGUGUACC AUUCAAAAAA GAUCAAUGCA AUAUUCGGCC   4080

CGUUGUUUAG UGAGCUUACU AGGCAAUUAC UGGACAGUGU UGAUUCGAGC AGAUUUUUGU   4140
```

-continued

```
UUUUCACAAG AAAGACACCA GCGCAGAUUG AGGAUUUCUU CGGAGAUCUC GACAGUCAUG   4200

UGCCGAUGGA UGUCUUGGAG CUGGAUAUAU CAAAAUACGA CAAAUCUCAG AAUGAAUUCC   4260

ACUGUGCAGU AGAAUACGAG AUCGGCGAA GAUUGGGUUU UGAAGACUUC UUGGGAGAAG    4320

UUUGGAAACA AGGGCAUAGA AAGACCACCC UCAAGGAUUA UACCGCAGGU AUAAAAACUU   4380

GCAUCUGGUA UCAAGAAAG AGCGGGACG UCACGACGUU CAUUGGAAAC ACUGUGAUCA    4440

UUGCUGCAUG UUUGGCCUCG AUGCUUCCGA UGGAGAAAAU AAUCAAAGGA GCCUUUUGCG   4500

GUGACGAUAG UCUGCUGUAC UUUCCAAAGG GUUGUGAGUU UCCGGAUGUG CAACACUCCG   4560

CGAAUCUUAU GUGGAAUUUU GAAGCAAAAC UGUUUAAAAA ACAGUAUGGA UACUUUUGCG   4620

GAAGAUAUGU AAUACAUCAC GACAGAGGAU GCAUUGUGUA UUACGAUCCC CUAAAGUUGA   4680

UCUCGAAACU GGUGCUAAA CACAUCAAGG AUUGGGAACA CUGGAGGAG UUCAGAAGGU    4740

CUCUUUGUGA UGUUGCUGUU UCGUUGAACA AUUGUGCGUA UUACACACAG UUGGACGACG   4800

CUGUAUGGGA GGUUCAUAAG ACCGCCCCUC CAGGUUCGUU UGUUUAUAAA AGUCUGGUGA   4860

AGUAUUUGUC UGAUAAAGUU CUUUUUAGAA GUUUGUUUAU AGAUGGCUCU AGUUGUUAAA   4920

GGAAAAGUGA AUAUCAAUGA GUUUAUCGAC CUGUCAAAAA UGGAGAAGAU CUUACCGUCG   4980

AUGUUUACCC CUGUAAAGAG UGUUAUGUGU UCCAAAGUUG AUAAAAUAAU GGUUCAUGAG   5040

AAUGAGUCAU UGUCAGAGGU GAACCUUCUU AAAGGAGUUA AGCUUAUUGA UAGUGGAUAC   5100

GUCUGUUUAG CCGGUUUGGU CGUCACGGGC GAGUGGAACU UGCCUGACAA UUGCAGAGGA   5160

GGUGUGAGCG UGUGUCUGGU GGACAAAAGG AUGGAAAGAG CCGACGAGGC CACUCUCGGA   5220

UCUUACUACA CAGCAGCUGC AAAGAAAAGA UUUCAGUUCA AGGUCGUUCC CAAUUAUGCU   5280

AUAACCACCC AGGACGCGAU GAAAAACGUC UGGCAAGUUU UAGUUAAUAU UAGAAAUGUG   5340

AAGAUGUCAG CGGGUUUCUG UCCGCUUUCU CUGGAGUUUG UGUCGGUGUG UAUUGUUUAU   5400

AGAAAUAAUA UAAAAUUAGG UUUGAGAGAG AAGAUUACAA ACGUGAGAGA CGGAGGGCCC   5460

AUGGAACUUA CAGAAGAAGU CGUUGAUGAG UUCAUGGAAG AUGUCCCUAU GUCGAUCAGG   5520

CUUGCAAAGU UUCGAUCUCG AACCGGAAAA AAGAGUGAUG UCCGCAAAGG GAAAAAUAGU   5580

AGUAAUGAUC GGUCAGUGCC GAACAAGAAC UAUAGAAAUG UUAAGGAUUU UGGAGGAAUG   5640

AGUUUUAAAA AGAAUAAUUU AAUCGAUGAU GAUUCGGAGG CUACUGUCGC CGAAUCGGAU   5700

UCGUUUUAAA UAUGUCUUAC AGUAUCACUA CUCCAUCUCA GUUCGUGUUC UUGUCAUCAG   5760

CGUGGGCCGA CCCAAUAGAG UUAAUUAAUU UAUGUACUAA UGCCUUAGGA AAUCAGUUUC   5820

AAACACAACA AGCUCGAACU GUCGUUCAAA GACAAUUCAG UGAGGUGUGG AAACCUUCAC   5880

CACAAGUAAC UGUUAGGUUC CCUGACAGUG ACUUUAAGGU GUACAGGUAC AAUGCGGUAU   5940

UAGACCCGCU AGUCACAGCA CUGUUAGGUG CAUUCGACAC UAGAAAUAGA AUAAUAGAAG   6000

UUGAAAAUCA GGCGAACCCC ACGACUGCCG AGACGUUAGA UGCUACUCGU AGAGUAGACG   6060

ACGCAACGGU GGCCAUAAGG AGCGCGAUAA AUAAUUUAAU AGUAGAAUUG AUCAGAGGAA   6120

CCGGAUCUUA UAAUCGGAGC UCUUUCGAGA GCUCUUCUGG UUUGGUUUGG ACCUCUGGUC   6180

CUGCAACUUG AGGUAGUCAA GAUGCAUAAU AAAUAACGGA UUGUGUCCGU AAUCACACGU   6240

GGUGCGUACG AUAACGCAUA GUGUUUUUCC CUCCACUUAA AUCGAAGGGU UGUGUCUUGG   6300

AUCGCGCGGG UCAAAUGUAU AUGGUUCAUA UACAUCCGCA GGCACGUAAU AAAGCGAGGG   6360

GUUCGAAUCC CCCCGUUACC CCCGGUAGGG GCCCA                              6395
```

(2) INFORMATION FOR SEQ ID NO:2:

(i) SEQUENCE CHARACTERISTICS:
    (A) LENGTH: 6439 base pairs
    (B) TYPE: nucleic acid
    (C) STRANDEDNESS: single
    (D) TOPOLOGY: unknown (ii) MOLECULE TYPE: Genomic RNA (xi) SEQUENCE DESCRIPTION: SEQ ID NO:2:

```
GUAUUUUUAC AACAAUUACC AACAACAACA AACAACAAAC AACAUUACAA UUACUAUUUA    60

CAAUUACAAU GGCAUACACA CAGACAGCUA CCACAUCAGC UUUGCUGGAC ACUGUCCGAG   120

GAAACAACUC CUUGGUCAAU GAUCUAGCAA AGCGUCGUCU UUACGACACA GCGGUUGAAG   180

AGUUUAACGC UCGUGACCGC AGGCCCAAGG UGAACUUUUC AAAAGUAAUA AGCGAGGAGC   240

AGACGCUUAU UGCUACCCGG GCGUAUCCAG AAUUCCAAAU UACAUUUUAU AACACGCAAA   300

AUGCCGUGCA UUCGCUUGCA GGUGGAUUGC GAUCUUUAGA ACUGGAAUAU CUGAUGAUGC   360

AAAUUCCCUA CGGAUCAUUG ACUUAUGACA UAGGCGGGAA UUUUGCAUCG CAUCUGUUCA   420

AGGGACGAGC AUAUGUACAC UGCUGCAUGC CCAACCUGGA CGUUCGAGAC AUCAUGCGGC   480

ACGAAGGCCA GAAAGACAGU AUUGAACUAU ACCUUUCUAG GCUAGAGAGA GGGGGGAAAA   540

CAGUCCCCAA CUUCCAAAAG GAAGCAUUUG ACAGAUACGC AGAAAUUCCU GAAGACGCUG   600

UCUGUCACAA UACUUUCCAG ACAAUGCGAC AUCAGCCGAU GCAGCAAUCA GGCAGAGUGU   660

AUGCCAUUGC GCUACACAGC AUAUAUGACA UACCAGCCGA UGAGUUCGGG GCGGCACUCU   720

UGAGGAAAAA UGUCCAUACG UGCUAUGCCG CUUUCCACUU CUCCGAGAAC CUGCUUCUUG   780

AAGAUUCAUA CGUCAAUUUG GACGAAAUCA ACGCGUGUUU UUCGCGCGAU GGAGACAAGU   840

UGACCUUUUC UUUUGCAUCA GAGAGUACUC UUAAUUAUUG UCAUAGUUAU UCUAAUAUUC   900

UUAAGUAUGU GUGCAAAACU UACUUCCCGG CCUCUAAUAG AGAGGUUUAC AUGAAGGAGU   960

UUUUAGUCAC CAGAGUUAAU ACCGGUUUUU GUAAGUUUUC UAGAAUAGAU ACUUUUCUUU  1020

UGUACAAAGG UGUGGCCCAU AAAAGUGUAG AUAGUGAGCA GUUUUAUACU GCAAUGGAAG  1080

ACGCAUGGCA UUACAAAAAG ACUCUUGCAA UGCAACAG CGAGAGAAUC CUCCUUGAGG  1140

AUUCAUCAUC AGUCAAUUAC UGGUUUCCCA AAAUGAGGGA UAUGGUCAUC GUACCAUUAU  1200

UCGACAUUUC UUUGGAGACU AGUAAGAGGA CGCGCAAGGA AGUCUUAGUG UCCAAGGAUU  1260

UCGUGUUUAC AGUGCUUAAC CACAUUCGAA CAUACCAGGC GAAAGCUCUU ACAUACGCAA  1320

AUGUUUUGUC CCUUGUCGAA UCGAUUCGAU CGAGGGUAAU CAUUAACGGU GUGACAGCGA  1380

GGUCCGAAUG GGAUGUGGAC AAAUCUUUGU UACAAUCCUU GUCCAUGACG UUUUACCUGC  1440

AUACUAAGCU UGCCGUUCUA AAGGAUGACU UACUGAUUAG CAAGUUUAGU CUCGGUUCGA  1500

AAACGGUGUG CCAGCAUGUG UGGGAUGAGA UUUCGCUGGC GUUUGGGAAC GCAUUUCCCU  1560

CCGUGAAAGA GAGACUCUUG AACAGGAAAC UUAUCAGAGU GGCAGGCGAC GCAUUAGAGA  1620

UCAGGGUGCC UGAUCUAUAU GUGACCUUCC ACGACAGAUU AGUGACUGAG UACAAGGCCU  1680

CUGUGGACAU GCCUGCGCUU GACAUUAGGA AGAAGAUGGA AGAAACGGAA GUGAUGUACA  1740

AUGCACUUUC AGAGUUAUCG GUGUUAAGGG AGCUGACAA AUUCGAUGUU GAUGUUUUUU  1800

CCCAGAUGUG CCAAUCUUUG GAAGUUGACC CAAUGACGGC AGCGAAGGUU AUAGUCGCGG  1860

UCAUGAGCAA UGAGAGCGGU CUGACUCUCA CAUUUGAACG ACCUACUGAG GCGAAUGUUG  1920

CGCUAGCUUU ACAGGAUCAA GAGAAGGCUU CAGAAGGUGC AUUGGUAGUU ACCUCAAGAG  1980

AAGUUGAAGA ACCGUCCAUG AAGGGUUCGA UGGCCAGAGG AGAGUUACAA UUAGCUGGUC  2040

UUGCUGGAGA UCAUCCGGAG UCGUCCUAUU CUAAGAACGA GGAGAUAGAG UCUUUAGAGC  2100
```

-continued

```
AGUUUCAUAU GGCGACGGCA GAUUCGUUAA UUCGUAAGCA GAUGAGCUCG AUUGUGUACA   2160

CGGGUCCGAU UAAAGUUCAG CAAAUGAAAA ACUUUAUCGA UAGCCUGGUA GCAUCACUAU   2220

CUGCUGCGGU GUCGAAUCUC GUCAAGAUCC UCAAAGAUAC AGCUGCUAUU GACCUUGAAA   2280

CCCGUCAAAA GUUUGGAGUC UUGGAUGUUG CAUCUAGGAA GUGGUUAAUC AAACCAACGG   2340

CCAAGAGUCA UGCAUGGGGU GUUGUUGAAA CCCACGCGAG GAAGUAUCAU GUGGCGCUUU   2400

UGGAAUAUGA UGAGCAGGGU GUGGUGACAU GCGAUGAUUG GAGAAGAGUA GCUGUUAGCU   2460

CUGAGUCUGU UGUUUAUUCC GACAUGGCGA AACUCAGAAC UCUGCGCAGA CUGCUUCGAA   2520

ACGGAGAACC GCAUGUCAGU AGCGCAAAGG UUGUUCUUGU GGACGGAGUU CCGGGCUGUG   2580

GAAAAACCAA AGAAAUUCUU UCCAGGGUUA AUUUGAUGA AGAUCUAAUU UUAGUACCUG    2640

GGAAGCAAGC CGCGGAAAUG AUCAGAAGAC GUGCGAAUUC CUCAGGGAUU AUUGUGGCCA   2700

CGAAGGACAA CGUUAAAACC GUUGAUUCUU UCAUGAUGAA UUUUGGGAAA AGCACACGCU   2760

GUCAGUUCAA GAGGUUAUUC AUUGAUGAAG GGUUGAUGUU GCAUACUGGU UGUGUUAAUU   2820

UUCUUGUGGC GAUGUCAUUG UGCGAAAUUG CAUAUGUUUA CGGAGACACA CAGCAGAUUC   2880

CAUACAUCAA UAGAGUUUCA GGAUUCCCGU ACCCCGCCCA UUUUGCCAAA UUGGAAGUUG   2940

ACGAGGUGGA GACACGCAGA ACUACUCUCC GUUGUCCAGC CGAUGUCACA CAUUAUCUGA   3000

ACAGGAGAUA UGAGGGCUUU GUCAUGAGCA CUUCUUCGGU UAAAAAGUCU GUUUCGCAGG   3060

AGAUGGUCGG CGGAGCCGCC GUGAUCAAUC CGAUCUCAAA ACCCUUGCAU GGCAAGAUCC   3120

UGACUUUUAC CCAAUCGGAU AAAGAAGCUC UGCUUUCAAG AGGGUAUUCA GAUGUUCACA   3180

CUGUGCAUGA AGUGCAAGGC GAGACAUACU CUGAUGUUUC ACUAGUUAGG UUAACCCCUA   3240

CACCAGUCUC CAUCAUUGCA GGAGACAGCC CACAUGUUUU GGUCGCAUUG UCAAGGCACA   3300

CCUGUUCGCU CAAGUACUAC ACUGUUGUUA UGGAUCCUUU AGUUAGUAUC AUUAGAGAUC   3360

UAGAGAAACU UAGCUCGUAC UUGUUAGAUA UGUAUAAGGU CGAUGCAGGA ACACAAUAGC   3420

AAUUACAGAU UGACUCGGUG UUCAAAGGUU CCAAUCUUUU UGUUGCAGCG CCAAAGACUG   3480

GUGAUAUUUC UGAUAUGCAG UUUUACUAUG AUAAGUGUCU CCCAGGCAAC AGCACCAUGA   3540

UGAAUAAUUU UGAUGCUGUU ACCAUGAGGU UGACUGACAU UUCAUUGAAU GUCAAAGAUU   3600

GCAUAUUGGA UAUGUCUAAG UCUGUUCGUG CGCCUAAGGA UCAAAUCAAA CCACUAAUAC   3660

CUAUGGUACG AACGGCGGCA GAAAUGCCAC GCCAGACUGG ACUAUUGGAA AAUUUAGUGG   3720

CGAUGAUUAA AGAAACUUUU AACGCACCCG AGUUGUCUGG CAUCAUUGAU AUUGAAAAUA   3780

CUGCAUCUUU GGUUGUAGAU AAGUUUUUUG AUAGUUAUUU GCUUAAAGAA AAAAGAAAAC   3840

CAAAUAAAAA UGUUUCUUUG UUCAGUAGAG AGUCUCUCAA UAGAUGGUUA GAAAAGCAGG   3900

AACAGGUAAC AAUAGGCCAG CUCGCAGAUU UUGAUUUUGU GGAUUUGCCA GCAGUUGAUC   3960

AGUACAGACA CAUGAUUAAA GCACAACCCA AACAAAAGUU GGACACUUCA AUCCAAACGG   4020

AGUACCCGGC UUUGCAGACG AUUGUGUACC AUUCAAAAAA GAUCAAUGCA AUAUUCGGCC   4080

CGUUGUUUAG UGAGCUUACU AGGCAAUUAC UGGACAGUGU UGAUUCGAGC AGAUUUUUGU   4140

UUUUCACAAG AAAGACACCA GCGCAGAUUG AGGAUUUCUU CGGAGAUCUC GACAGUCAUG   4200

UGCCGAUGGA UGUCUUGGAG CUGGAUAUAU CAAAAUACGA CAAAUCUCAG AAUGAAUUCC   4260

ACUGUGCAGU AGAAUACGAG AUCGGCGAA GAUUGGGUUU GAAGACUUC UUGGGAGAAG     4320

UUUGGAAACA AGGGCAUAGA AAGACCACCC UCAAGGAUUA UACCGCAGGU AUAAAAACUU   4380

GCAUCUGGUA UCAAAGAAAG AGCGGGGACG UCACGACGUU CAUUGGAAAC ACUGUGAUCA   4440
```

-continued

```
UUGCUGCAUG UUUGGCCUCG AUGCUUCCGA UGGAGAAAAU AAUCAAAGGA GCCUUUUGCG    4500

GUGACGAUAG UCUGCUGUAC UUUCCAAAGG GUUGUGAGUU UCCGGAUGUG CAACACUCCG    4560

CGAAUCUUAU GUGGAAUUUU GAAGCAAAAC UGUUUAAAAA ACAGUAUGGA UACUUUUGCG    4620

GAAGAUAUGU AAUACAUCAC GACAGAGGAU GCAUUGUGUA UUACGAUCCC CUAAAGUUGA    4680

UCUCGAAACU GGUGCUAAAA CACAUCAAGG AUUGGGAACA CUGGAGGAG UUCAGAAGGU     4740

CUCUUUGUGA UGUUGCUGUU UCGUUGAACA AUGUGCGUA UUACACACAG UUGGACGACG     4800

CUGUAUGGGA GGUUCAUAAG ACCGCCCCUC CAGGUUCGUU UGUUUAUAAA AGUCUGGUGA    4860

AGUAUUUGUC UGAUAAAGUU CUUUUUAGAA GUUUGUUUAU AGAUGGCUCU AGUUGUUAAA    4920

GGAAAAGUGA AUAUCAAUGA GUUUAUCGAC CUGUCAAAAA UGGAGAAGAU CUUACCGUCG    4980

AUGUUUACCC CUGUAAAGAG UGUUAUGUGU UCCAAAGUUG AUAAAAUAAU GGUUCAUGAG    5040

AAUGAGUCAU UGUCAGAGGU GAACCUUCUU AAAGGAGUUA AGCUUAUUGA UAGUGGAUAC    5100

GUCUGUUUAG CCGGUUUGGU CGUCACGGGC GAGUGGAACU UGCCUGACAA UUGCAGAGGA    5160

GGUGUGAGCG UGUGUCUGGU GGACAAAAGG AUGGAAAGAG CCGACGAGGC CACUCUCGGA    5220

UCUUACUACA CAGCAGCUGC AAAGAAAAGA UUUCAGUUCA AGGUCGUUCC CAAUUAUGCU    5280

AUAACCACCC AGGACGCGAU GAAAAACGUC UGGCAAGUUU AGUUAAUAU UAGAAAUGUG     5340

AAGAUGUCAG CGGGUUUCUG UCCGCUUUCU CUGGAGUUUG UGUCGGUGUG UAUUGUUUAU    5400

AGAAAUAAUA UAAAAUUAGG UUUGAGAGAG AAGAUUACAA ACGUGAGAGA CGGAGGGCCC    5460

AUGGAACUUA CAGAAGAAGU CGUUGAUGAG UUCAUGGAAG AUGUCCCUAU GUCGAUCAGG    5520

CUUGCAAAGU UUCGAUCUCG AACCGGAAAA AAGAGUGAUG UCCGCAAAGG GAAAAAUAGU    5580

AGUAAUGAUC GGUCAGUGCC GAACAAGAAC UAUAGAAAUG UUAAGGAUUU UGGAGGAAUG    5640

AGUUUUAAAA AGAAUAAUUU AAUCGAUGAU GAUUCGGAGG CUACUGUCGC CGAAUCGGAU    5700

UCGUUUUAAA UAUGCUUAC AGUAUCACUA CUCCAUCUCA GUUCGUGUUC UUGUCAUCAG     5760

CGUGGGCCGA CCCAAUAGAG UUAAUUAAUU UAUGUACUAA UGCCUUAGGA AAUCAGUUUC    5820

AAACACAACA AGCUCGAACU GUCGUUCAAA GACAAUUCAG UGAGGUGUGG AAACCUUCAC    5880

CACAAGUAAC UGUUAGGUUC CCUGACAGUG ACUUUAAGGU GUACAGGUAC AAUGCGGUAU    5940

UAGACCCGCU AGUCACAGCA CUGUUAGGUG CAUUCGACAC UAGAAAUAGA AUAAUAGAAG    6000

UUGAAAAUCA GGCGAACCCC ACGACUGCCG AAACGUUAGA UGCUACUCGU AGAGUAGACG    6060

ACGCAACGGU GGCCAUAAGG AGCGCGAUAA AUAAUUUAAU AGUAGAAUUG AUCAGAGGAA    6120

CCGGAUCUUA UAAUCGGAGC UCUUUCGAGA GCUCUUCUGG UUUGGUUUGG ACCUCUGGUC    6180

CUGCAACCUA GCAAUUACAA GGUCCAGGUG CACCUCAAGG UCCUGGAGCU CCCUAGGUAG    6240

UCAAGAUGCA UAAUAAAUAA CGGAUUGUGU CCGUAAUCAC ACGUGGUGCG UACGAUAACG    6300

CAUAGUGUUU UUCCCUCCAC UUAAAUCGAA GGGUUGUGUC UUGGAUCGCG CGGGUCAAAU    6360

GUAUAUGGUU CAUAUACAUC CGCAGGCACG UAAUAAAGCG AGGGGUUCGA AUCCCCCCGU    6420

UACCCCCGGU AGGGGCCCA                                                6439
```

(2) INFORMATION FOR SEQ ID NO:3:

(i) SEQUENCE CHARACTERISTICS:
        (A) LENGTH: 6425 base pairs
        (B) TYPE: nucleic acid
        (C) STRANDEDNESS: single
        (D) TOPOLOGY: unknown (ii) MOLECULE TYPE: Genomic RNA (xi) SEQUENCE DESCRIPTION: SEQ ID NO:3:

```
GUAUUUUUAC AACAAUUACC AACAACAACA AACAACAAAC AACAUUACAA UUACUAUUUA      60

CAAUUACAAU GGCAUACACA CAGACAGCUA CCACAUCAGC UUUGCUGGAC ACUGUCCGAG     120

GAAACAACUC CUUGGUCAAU GAUCUAGCAA AGCGUCGUCU UUACGACACA GCGGUUGAAG     180

AGUUUAACGC UCGUGACCGC AGGCCCAAGG UGAACUUUUC AAAAGUAAUA AGCGAGGAGC     240

AGACGCUUAU UGCUACCCGG GCGUAUCCAG AAUUCCAAAU UACAUUUUAU AACACGCAAA     300

AUGCCGUGCA UUCGCUUGCA GGUGGAUUGC GAUCUUUAGA ACUGGAAUAU CUGAUGAUGC     360

AAAUUCCCUA CGGAUCAUUG ACUUAUGACA UAGGCGGGAA UUUUGCAUCG CAUCUGUUCA     420

AGGGACGAGC AUAUGUACAC UGCUGCAUGC CCAACCUGGA CGUUCGAGAC AUCAUGCGGC     480

ACGAAGGCCA GAAAGACAGU AUUGAACUAU ACCUUUCUAG GCUAGAGAGA GGGGGGAAAA     540

CAGUCCCCAA CUUCCAAAAG GAAGCAUUUG ACAGAUACGC AGAAAUUCCU GAAGACGCUG     600

UCUGUCACAA UACUUUCCAG ACAAUGCGAC AUCAGCCGAU GCAGCAAUCA GGCAGAGUGU     660

AUGCCAUUGC GCUACACAGC AUAUAUGACA UACCAGCCGA UGAGUUCGGG GCGGCACUCU     720

UGAGGAAAAA UGUCCAUACG UGCUAUGCCG CUUUCCACUU UCUGAGAAC CUGCUUCUUG      780

AAGAUUCAUA CGUCAAUUUG GACGAAAUCA ACGCGUGUUU UUCGCGCGAU GGAGACAAGU     840

UGACCUUUUC UUUUGCAUCA GAGAGUACUC UUAAUUAUUG UCAUAGUUAU UCUAAUAUUC     900

UUAAGUAUGU GUGCAAAACU UACUUCCCGG CCUCUAAUAG AGAGGUUUAC AUGAAGGAGU     960

UUUUAGUCAC CAGAGUUAAU ACCUGGUUUU GUAAGUUUUC UAGAAUAGAU ACUUUUCUUU    1020

UGUACAAAGG UGUGGCCCAU AAAAGUGUAG AUAGUGAGCA GUUUUAUACU GCAAUGGAAG    1080

ACGCAUGGCA UUACAAAAAG ACUCUUGCAA UGUGCAACAG CGAGAGAAUC CUCCUUGAGG    1140

AUUCAUCAUC AGUCAAUUAC UGGUUUCCCA AAAUGAGGGA UAUGGUCAUC GUACCAUUAU    1200

UCGACAUUUC UUUGGAGACU AGUAAGAGGA CGCGCAAGGA AGUCUUAGUG UCCAAGGAUU    1260

UCGUGUUUAC AGUGCUUAAC CACAUUCGAA CAUACCAGGC GAAAGCUCUU ACAUACGCAA    1320

AUGUUUUGUC CUUUGUCGAA UCGAUUCGAU CGAGGGUAAU CAUUAACGGU GUGACAGCGA    1380

GGUCCGAAUG GGAUGUGGAC AAAUCUUUGU UACAAUCCUU GUCCAUGACG UUUUACCUGC    1440

AUACUAAGCU UGCCGUUCUA AAGGAUGACU UACUGAUUAG CAAGUUUAGU CUCGGUUCGA    1500

AAACGGUGUG CCAGCAUGUG UGGGAUGAGA UUUCGCUGGC GUUUGGGAAC GCAUUUCCCU    1560

CCGUGAAAGA GAGGCUCUUG AACAGGAAAC UUAUCAGAGU GGCAGGCGAC GCAUUAGAGA    1620

UCAGGGUGCC UGAUCUAUAU GUGACCUUCC ACGACAGAUU AGUGACUGAG UACAAGGCCU    1680

CUGUGGACAU GCCUGCGCUU GACAUUAGGA AGAAGAUGGA AGAAACGAA GUGAUGUACA     1740

AUGCACUUUC AGAGUUAUCG GUGUUAAGGG AGUCUGACAA AUUCGAUGUU GAUGUUUUUU    1800

CCCAGAUGUG CCAAUCUUUG GAAGUUGACC CAAUGACGGC AGCGAAGGUU AUAGUCGCGG    1860

UCAUGAGCAA UGAGAGCGGU CUGACUCUCA CAUUUGAACG ACCUACUGAG GCGAAUGUUG    1920

CGCUAGCUUU ACAGGAUCAA GAGAAGGCUU CAGAAGGUGC UUUGGUAGUU ACCUCAAGAG    1980

AAGUUGAAGA ACCGUCCAUG AAGGGUUCGA UGGCCAGAGG AGAGUUACAA UUAGCUGGUC    2040

UUGCUGGAGA UCAUCCGGAG UCGUCCUAUU CUAAGAACGA GGAGAUAGAG UCUUUAGAGC    2100

AGUUUCAUAU GGCAACGGCA GAUUCGUUAA UUCGUAAGCA GAUGAGCUCG AUUGUGUACA    2160

CGGGUCCGAU UAAAGUUCAG CAAAUGAAAA ACUUUAUCGA UAGCCUGGUA GCAUCACUAU    2220

CUGCUGCGGU GUCGAAUCUC GUCAAGAUCC UCAAAGAUAC AGCUGCUAUU GACCUUGAAA    2280

CCCGUCAAAA GUUUGGAGUC UUGGAUGUUG CAUCUAGGAA GUGGUUAAUC AAACCAACGG    2340
```

```
CCAAGAGUCA UGCAUGGGGU GUUGUUGAAA CCCACGCGAG GAAGUAUCAU GUGGCGCUUU    2400

UGGAAUAUGA UGAGCAGGGU GUGGUGACAU GCGAUGAUUG GAGAAGAGUA GCUGUCAGCU    2460

CUGAGUCUGU UGUUUAUUCC GACAUGGCGA AACUCAGAAC UCUGCGCAGA CUGCUUCGAA    2520

ACGGAGAACC GCAUGUCAGU AGCGCAAAGG UUGUUCUUGU GGACGGAGUU CCGGGCUGUG    2580

GGAAAACCAA AGAAAUUCUU UCCAGGGUUA AUUUGAUGA AGAUCUAAUU UUAGUACCUG    2640

GGAAGCAAGC CGCGGAAAUG AUCAGAAGAC GUGCGAAUUC CUCAGGGAUU AUUGUGGCCA    2700

CGAAGGACAA CGUUAAAACC GUUGAUUCUU UCAUGAUGAA UUUUGGGAAA AGCACACGCU    2760

GUCAGUUCAA GAGGUUAUUC AUUGAUGAAG GGUUGAUGUU GCAUACUGGU UGUGUUAAUU    2820

UUCUUGUGGC GAUGUCAUUG UGCGAAAUUG CAUAUGUUUA CGGAGACACA CAGCAGAUUC    2880

CAUACAUCAA UAGAGUUUCA GGAUUCCCGU ACCCCGCCCA UUUUGCCAAA UUGGAAGUUG    2940

ACGAGGUGGA GACACGCAGA ACUACUCUCC GUUGUCCAGC CGAUGUCACA CAUUAUCUGA    3000

ACAGGAGAUA UGAGGGCUUU GUCAUGAGCA CUUCUUCGGU UAAAAAGUCU GUUUCGCAGG    3060

AGAUGGUCGG CGGAGCCGCC GUGAUCAAUC CGAUCUCAAA ACCCUUGCAU GGCAAGAUCC    3120

UGACUUUUAC CCAAUCGGAU AAAGAAGCUC UGCUUUCAAG AGGGUAUUCA GAUGUUCACA    3180

CUGUGCAUGA AGUCAAGGC GAGACAUACU CUGAUGUUUC ACUAGUUAGG UUAACCCCUA    3240

CACCAGUCUC CAUCAUUGCA GGAGACAGCC CACAUGUUUU GGUCGCAUUG UCAAGGCACA    3300

CCUGUUCGCU CAAGUACUAC ACUGUUGUUA UGGAUCCUUU AGUUAGUAUC AUUAGAGAUC    3360

UAGAGAAACU UAGCUCGUAC UUGUUAGAUA UGUAUAAGGU CGAUGCAGGA ACACAAUAGC    3420

AAUUACAGAU UGACUCGGUG UUCAAAGGUU CCAAUCUUUU UGUUGCAGCG CCAAAGACUG    3480

GUGAUAUUUC UGAUAUGCAG UUUUACUAUG AUAAGUGUCU CCCAGGCAAC AGCACCAUGA    3540

UGAAUAAUUU UGAUGCUGUU ACCAUGAGGU UGACUGACAU UUCAUUGAAU GUCAAAGAUU    3600

GCAUAUUGGA UAUGUCUAAG UCUGUUGCUG CGCCUAAGGA UCAAAUCAAA CCACUAAUAC    3660

CUAUGGUACG AACGGCGGCA GAAAUGCCAC GCCAGACUGG ACUAUUGGAA AAUUUAGUGG    3720

CGAUGAUUAA AAGGAACUUU AACGCACCCG AGUUGUCUGG CAUCAUUGAU AUUGAAAAUA    3780

CUGCAUCUUU AGUUGUAGAU AAGUUUUUUG AUAGUUAUUU GCUUAAAGAA AAAAGAAAAC    3840

CAAAUAAAAA UGUUUCUUUG UUCAGUAGAG AGUCUCUCAA UAGAUGGUUA GAAAAGCAGG    3900

AACAGGUAAC AAUAGGCCAG CUCGCAGAUU UUGAUUUUGU AGAUUUGCCA GCAGUUGAUC    3960

AGUACAGACA CAUGAUUAAA GCACAACCCA AGCAAAAAUU GGACACUUCA AUCCAAACGG    4020

AGUACCCGGC UUUGCAGACG AUUGUGUACC AUUCAAAAAA GAUCAAUGCA AUAUUUGGCC    4080

CGUUGUUUAG UGAGCUUACU AGGCAAUUAC UGGACAGUGU UGAUUCGAGC AGAUUUUUGU    4140

UUUUCACAAG AAAGACACCA GCGCAGAUUG AGGAUUUCUU CGGAGAUCUC GACAGUCAUG    4200

UGCCGAUGGA UGUCUUGGAG CUGGAUAUAU CAAAAUACGA CAAAUCUCAG AAUGAAUUCC    4260

ACUGUGCAGU AGAAUACGAG AUCUGGCGAA GAUUGGGUUU GAAGACUUC UUGGGAGAAG    4320

UUUGGAAACA AGGGCAUAGA AAGACCACCC UCAAGGAUUA UACCGCAGGU AUAAAAACUU    4380

GCAUCUGGUA UCAAAGAAAG AGCGGGGACG UCACGACGUU CAUUGGAAAC ACUGUGAUCA    4440

UUGCUGCAUG UUUGGCCUCG AUGCUUCCGA UGGAGAAAAU AAUCAAAGGA GCCUUUUGCG    4500

GUGACGAUAG UCUGCUGUAC UUUCCAAAGG GUUGUGAGUU CCGGAUGUG CAACACUCCG    4560

CGAAUCUUAU GUGGAAUUUU GAAGCAAAAC UGUUUAAAAA ACAGUAUGGA UACUUUUGCG    4620

GAAGAUAUGU AAUACAUCAC GACAGAGGAU GCAUUGUGUA UUACGAUCCC CUAAAGUUGA    4680
```

```
UCUCGAAACU UGGUGCUAAA CACAUCAAGG AUUGGGAACA CUUGGAGGAG UUCAGAAGGU    4740

CUCUUUGUGA UGUUGCUGUU UCGUUGAACA AUUGUGCGUA UUACACACAG UUGGACGACG    4800

CUGUAUGGGA GGUUCAUAAG ACCGCCCCUC CAGGUUCGUU UGUUAUAAAA AGUCUGGUGA    4860

AGUAUUUGUC UGAUAAAGUU CUUUUUAGAA GUUUGUUUAU AGAUGGCUCU AGUUGUUAAA    4920

GGAAAAGUGA AUAUCAAUGA GUUUAUCGAC CUGACAAAAA UGGAGAAGAU CUUACCGUCG    4980

AUGUUUACCC CUGUAAAGAG UGUUAUGUGU UCCAAGUUG AUAAAUAAU GGUUCAUGAG    5040

AAUGAGUCAU UGUCAGAGGU GAACCUUCUU AAAGGAGUUA AGCUUAUUGA UAGUGGAUAC    5100

GUCUGUUUAG CCGGUUUGGU CGUCACGGGC GAGUGGAACU UGCCUGACAA UUGCAGAGGA    5160

GGUGUGAGCG UGUGUCUGGU GGACAAAAGG AUGGAAAGAG CCGACGAGGC CACUCUCGGA    5220

UCUUACUACA CAGCAGCUGC AAAGAAAAGA UUUCAGUUCA AGGUCGUUCC CAAUUAUGCU    5280

AUAACCACCC AGGACGCGAU GAAAAACGUC UGGCAAGUUU UAGUUAAUAU UAGAAAUGUG    5340

AAGAUGUCAG CGGGUUUCUG UCCGCUUUCU CUGGAGUUUG UGUCGGUGUG UAUUGUUUAU    5400

AGAAAUAAUA UAAAAUUAGG UUUGAGAGAG AAGAUUACAA ACGUGAGAGA CGGAGGGCCC    5460

AUGGAACUUA CAGAAGAAGU CGUUGAUGAG UUCAUGGAAG AUGUCCCUAU GUCGAUCAGG    5520

CUUGCAAAGU UUCGAUCUCG AACCGGAAAA AAGAGUGAUG UCCGCAAAGG GAAAAAUAGU    5580

AGUAAUGAUC GGUCAGUGCC GAACAAGAAC UAUAGAAAUG UUAAGGAUUU UGGAGGAAUG    5640

AGUUUUAAAA AGAAUAAUUU AAUCGAUGAU GAUUCGGAGG CUACUGUCGC CGAAUCGGAU    5700

UCGUUUUAAA UAUGUCUUAC AGUAUCACUA CUCCAUCUCA GUUCGUGUUC UUGUCAUCAG    5760

CGUGGGCCGA CCCAAUAGAG UUAAUUAAUU UAUGUACUAA UGCCUUAGGA AAUCAGUUUC    5820

AAACACAACA AGCUCGAACU GUCGUUCAAA GACAAUUCAG UGAGGUGUGG AAACCUUCAC    5880

CACAAGUAAC UGUUAGGUUC CCUGCAGGCG AUCGGGCUGG UGACCGUGCA GGAGACAGAG    5940

ACUUUAAGGU GUACAGGUAC AAUGCGGUAU UAGACCCGCU AGUCACAGCA CUGUUAGGUG    6000

CAUUCGACAC UAGAAAUAGA AUAAUAGAAG UUGAAAAUCA GGCGAACCCC ACGACUGCCG    6060

AAACGUUAGA UGCUACUCGU AGAGUAGACG ACGCAACGGU GGCCAUAAGG AGCGCGAUAA    6120

AUAAUUUAAU AGUAGAAUUG AUCAGAGGAA CCGGAUCUUA UAAUCGGAGC UCUUUCGAGA    6180

GCUCUUCUGG UUUGGUUUGG ACCUCUGGUC CUGCAACUUG AGGUAGUCAA GAUGCAUAAU    6240

AAAUAACGGA UUGUGUCCGU AAUCACACGU GGUGCGUACG AUAACGCAUA GUGUUUUUCC    6300

CUCCACUUAA AUCGAAGGGU UGUGUCUUGG AUCGCGCGGG UCAAAUGUAU AUGGUUCAUA    6360

UACAUCCGCA GGCACGUAAU AAAGCGAGGG GUUCGAAUCC CCCCGUUACC CCCGGUAGGG    6420

GCCCA                                                               6425
```

(2) INFORMATION FOR SEQ ID NO:4:

(i) SEQUENCE CHARACTERISTICS:
        (A) LENGTH: 6475 base pairs
        (B) TYPE: nucleic acid
        (C) STRANDEDNESS: single
        (D) TOPOLOGY: unknown (ii) MOLECULE TYPE: Genomic RNA (xi) SEQUENCE DESCRIPTION: SEQ ID NO:4:

```
GUAUUUUUAC AACAAUUACC AACAACAACA AACAACAAAC AACAUUACAA UUACUAUUUA      60

CAAUUACAAU GGCAUACACA CAGACAGCUA CCACAUCAGC UUUGCUGGAC ACUGUCCGAG     120

GAAACAACUC CUUGGUCAAU GAUCUAGCAA AGCGUCGUCU UUACGACACA GCGGUUGAAG     180
```

```
AGUUUAACGC UCGUGACCGC AGGCCCAAGG UGAACUUUUC AAAAGUAAUA AGCGAGGAGC    240

AGACGCUUAU UGCUACCCGG GCGUAUCCAG AAUUCCAAAU UACAUUUUAU AACACGCAAA    300

AUGCCGUGCA UUCGCUUGCA GGUGGAUUGC GAUCUUUAGA ACUGGAAUAU CUGAUGAUGC    360

AAAUUCCCUA CGGAUCAUUG ACUUAUGACA UAGGCGGGAA UUUUGCAUCG CAUCUGUUCA    420

AGGGACGAGC AUAUGUACAC UGCUGCAUGC CCAACCUGGA CGUUCGAGAC AUCAUGCGGC    480

ACGAAGGCCA GAAAGACAGU AUUGAACUAU ACCUUUCUAG GCUAGAGAGA GGGGGGAAAA    540

CAGUCCCCAA CUUCCAAAAG GAAGCAUUUG ACAGAUACGC AGAAAUUCCU GAAGACGCUG    600

UCUGUCACAA UACUUUCCAG ACAAUGCGAC AUCAGCCGAU GCAGCAAUCA GGCAGAGUGU    660

AUGCCAUUGC GCUACACAGC AUAUAUGACA UACCAGCCGA UGAGUUCGGG GCGGCACUCU    720

UGAGGAAAAA UGUCCAUACG UGCUAUGCCG CUUUCCACUU UCUGAGAAC  CUGCUUCUUG    780

AAGAUUCAUA CGUCAAUUUG GACGAAAUCA ACGCGUGUUU UUCGCGCGAU GGAGACAAGU    840

UGACCUUUUC UUUUGCAUCA GAGAGUACUC UUAAUUAUUG UCAUAGUUAU UCUAAUAUUC    900

UUAAGUAUGU GUGCAAAACU UACUUCCCGG CCUCUAAUAG AGAGGUUUAC AUGAAGGAGU    960

UUUUAGUCAC CAGAGUUAAU ACCUGGUUUU GUAAGUUUUC UAGAAUAGAU ACUUUUCUUU   1020

UGUACAAAGG UGUGGCCCAU AAAAGUGUAG AUAGUGAGCA GUUUUAUACU GCAAUGGAAG   1080

ACGCAUGGCA UUACAAAAAG ACUCUUGCAA UGUGCAACAG CGAGAGAAUC CUCCUUGAGG   1140

AUUCAUCAUC AGUCAAUUAC UGGUUUCCCA AAAUGAGGGA UAUGGUCAUC GUACCAUUAU   1200

UCGACAUUUC UUUGGAGACU AGUAAGAGGA CGCGCAAGGA AGUCUUAGUG UCCAAGGAUU   1260

UCGUGUUUAC AGUGCUUAAC CACAUUCGAA CAUACCAGGC GAAAGCUCUU ACAUACGCAA   1320

AUGUUUUGUC CUUUGUCGAA UCGAUUCGAU CGAGGGUAAU CAUUAACGGU GUGACAGCGA   1380

GGUCCGAAUG GGAUGUGGAC AAAUCUUUGU UACAAUCCUU GUCCAUGACG UUUUACCUGC   1440

AUACUAAGCU UGCCGUUCUA AAGGAUGACU UACUGAUUAG CAAGUUUAGU CUCGGUUCGA   1500

AAACGGUGUG CCAGCAUGUG UGGGAUGAGA UUUCGCUGGC GUUUGGGAAC GCAUUUCCCU   1560

CCGUGAAAGA GAGGCUCUUG AACAGGAAAC UUAUCAGAGU GGCAGGCGAC GCAUUAGAGA   1620

UCAGGGUGCC UGAUCUAUAU GUGACCUUCC ACGACAGAUU AGUGACUGAG UACAAGGCCU   1680

CUGUGGACAU GCCUGCGCUU GACAUUAGGA AGAAGAUGGA AGAAACGGAA GUGAUGUACA   1740

AUGCACUUUC AGAGUUAUCG GUGUUAAGGG AGUCUGACAA AUUCGAUGUU GAUGUUUUUU   1800

CCCAGAUGUG CCAAUCUUUG GAAGUUGACC CAAUGACGGC AGCGAAGGUU AUAGUCGCGG   1860

UCAUGAGCAA UGAGAGCGGU CUGACUCUCA CAUUUGAACG ACCACUGAG GCGAAUGUUG    1920

CGCUAGCUUU ACAGGAUCAA GAGAAGGCUU CAGAAGGUGC UUUGGUAGUU ACCUCAAGAG   1980

AAGUUGAAGA ACCGUCCAUG AAGGGUUCGA UGGCCAGAGG AGAGUUACAA UUAGCUGGUC   2040

UUGCUGGAGA UCAUCCGGAG UCGUCCUAUU CUAAGAACGA GGAGAUAGAG UCUUUAGAGC   2100

AGUUUCAUAU GGCAACGGCA GAUUCGUUAA UUCGUAAGCA GAUGAGCUCG AUUGUGUACA   2160

CGGGUCCGAU UAAAGUUCAG CAAAUGAAAA ACUUUAUCGA UAGCCUGGUA GCAUCACUAU   2220

CUGCUGCGGU GUCGAAUCUC GUCAAGAUCC UCAAAGAUAC AGCUGCUAUU GACCUUGAAA   2280

CCCGUCAAAA GUUUGGAGUC UUGGAUGUUG CAUCUAGGAA UGGGUUAAUC AAACCAACGG   2340

CCAAGAGUCA UGCAUGGGGU GUUGUUGAAA CCCACGCGAG GAAGUAUCAU GUGGCGCUUU   2400

UGGAAUAUGA UGAGCAGGGU GUGGUGACAU GCGAUGAUUG GAGAAGAGUA GCUGUCAGCU   2460

CUGAGUCUGU UGUUUAUUCC GACAUGGCGA AACUCAGAAC UCUGCGCAGA CUGCUUCGAA   2520

ACGGAGAACC GCAUGUCAGU AGCGCAAAGG UUGUUCUUGU GGACGGAGUU CCGGGCUGUG   2580
```

```
GGAAAACCAA AGAAAUUCUU UCCAGGGUUA AUUUUGAUGA AGAUCUAAUU UUAGUACCUG      2640

GGAAGCAAGC CGCGGAAAUG AUCAGAAGAC GUGCGAAUUC CUCAGGGAUU AUUGUGGCCA      2700

CGAAGGACAA CGUUAAAACC GUUGAUUCUU UCAUGAUGAA UUUUGGGAAA AGCACACGCU      2760

GUCAGUUCAA GAGGUUAUUC AUUGAUGAAG GGUUGAUGUU GCAUACUGGU UGUGUUAAUU      2820

UUCUUGUGGC GAUGUCAUUG UGCGAAAUUG CAUAUGUUUA CGGAGACACA CAGCAGAUUC      2880

CAUACAUCAA UAGAGUUUCA GGAUUCCCGU ACCCCGCCCA UUUUGCCAAA UUGGAAGUUG      2940

ACGAGGUGGA GACACGCAGA ACUACUCUCC GUUGUCCAGC CGAUGUCACA CAUUAUCUGA      3000

ACAGGAGAUA UGAGGGCUUU GUCAUGAGCA CUUCUUCGGU UAAAAAGUCU GUUUCGCAGG      3060

AGAUGGUCGG CGGAGCCGCC GUGAUCAAUC CGAUCUCAAA ACCCUUGCAU GGCAAGAUCC      3120

UGACUUUUAC CCAAUCGGAU AAAGAAGCUC UGCUUUCAAG AGGGUAUUCA GAUGUUCACA      3180

CUGUGCAUGA AGUCAAGGCA GAGACAUACU CUGAUGUUUC ACUAGUUAGG UUAACCCCUA      3240

CACCAGUCUC CAUCAUUGCA GGAGACAGCC CACAUGUUUU GGUCGCAUUG UCAAGGCACA      3300

CCUGUUCGCU CAAGUACUAC ACUGUUGUUA UGGAUCCUUU AGUUAGUAUC AUUAGAGAUC      3360

UAGAGAAACU UAGCUCGUAC UUGUUAGAUA UGUAUAAGGU CGAUGCAGGA ACACAAUAGC      3420

AAUUACAGAU UGACUCGGUG UUCAAAGGUU CCAAUCUUUU UGUUGCAGCG CCAAAGACUG      3480

GUGAUAUUUC UGAUAUGCAG UUUUACUAUG AUAAGUGUCU CCCAGGCAAC AGCACCAUGA      3540

UGAAUAAUUU UGAUGCUGUU ACCAUGAGGU UGACUGACAU UUCAUUGAAU GUCAAAGAUU      3600

GCAUAUUGGA UAUGUCUAAG UCUGUUGCUG CGCCUAAGGA UCAAAUCAAA CCACUAAUAC      3660

CUAUGGUACG AACGGCGGCA GAAAUGCCAC GCCAGACUGG ACUAUUGGAA AAUUUAGUGG      3720

CGAUGAUUAA AAGGAACUUU AACGCACCCG AGUUGUCUGG CAUCAUUGAU AUUGAAAAUA      3780

CUGCAUCUUU AGUUGUAGAU AAGUUUUUUG AUAGUAUUU GCUUAAAGAA AAAAGAAAAC      3840

CAAAUAAAAA UGUUUCUUUG UUCAGUAGAG AGUCUCUCAA UAGAUGGUUA GAAAAGCAGG      3900

AACAGGUAAC AAUAGGCCAG CUCGCAGAUU UUGAUUUUGU AGAUUUGCCA GCAGUUGAUC      3960

AGUACAGACA CAUGAUUAAA GCACAACCCA AGCAAAAAUU GGACACUUCA AUCCAAACGG      4020

AGUACCCGGC UUUGCAGACG AUUGUGUACC AUUCAAAAAA GAUCAAUGCA AUAUUUGGCC      4080

CGUUGUUUAG UGAGCUUACU AGGCAAUUAC UGGACAGUGU UGAUUCGAGC AGAUUUUUGU      4140

UUUUCACAAG AAAGACACCA GCGCAGAUUG AGGAUUUCUU CGGAGAUCUC GACAGUCAUG      4200

UGCCGAUGGA UGUCUUGGAG CUGGAUAUAU CAAAAUACGA CAAAUCUCAG AAUGAAUUCC      4260

ACUGUGCAGU AGAAUACGAG AUCGGCGAA GAUUGGGUUU UGAAGACUUC UUGGGAGAAG      4320

UUUGGAAACA AGGGCAUAGA AAGACCACCC UCAAGGAUUA UACCGCAGGU AUAAAAACUU      4380

GCAUCUGGUA UCAAAGAAAG AGCGGGACG UCACGACGUU CAUUGGAAAC ACUGUGAUCA      4440

UUGCUGCAUG UUUGGCCUCG AUGCUUCCGA UGGAGAAAAU AAUCAAAGGA GCCUUUUGCG      4500

GUGACGAUAG UCUGCUGUAC UUUCCAAAGG GUUGUGAGUU UCCGGAUGUG CAACACUCCG      4560

CGAAUCUUAU GUGGAAUUUU GAAGCAAAAC UGUUUAAAAA ACAGUAUGGA UACUUUUGCG      4620

GAAGAUAUGU AAUACAUCAC GACAGAGGAU GCAUUGUGUA UUACGAUCCC CUAAAGUUGA      4680

UCUCGAAACU UGGUGCUAAA CACAUCAAGG AUUGGGAACA CUUGGAGGAG UUCAGAAGGU      4740

CUCUUUGUGA UGUUGCUGUU UCGUUGAACA AUUGUGCGUA UUACACACAG UUGGACGACG      4800

CUGUAUGGGA GGUUCAUAAG ACCGCCCCUC CAGGUUCGUU UGUUUAUAAA AGUCUGGUGA      4860

AGUAUUUGUC UGAUAAAGUU CUUUUUAGAA GUUUGUUUAU AGAUGGCUCU AGUUGUUAAA      4920
```

```
GGAAAAGUGA AUAUCAAUGA GUUUAUCGAC CUGACAAAAA UGGAGAAGAU CUUACCGUCG    4980

AUGUUUACCC CUGUAAAGAG UGUUAUGUGU UCCAAAGUUG AUAAAAUAAU GGUUCAUGAG    5040

AAUGAGUCAU UGUCAGAGGU GAACCUUCUU AAAGGAGUUA AGCUAAUUGA UAGUGGAUAC    5100

GUCUGUUUAG CCGGUUUGGU CGUCACGGGC GAGUGGAACU UGCCUGACAA UUGCAGAGGA    5160

GGUGUGAGCG UGUGUCUGGU GGACAAAAGG AUGGAAAGAG CCGACGAGGC CACUCUCGGA    5220

UCUUACUACA CAGCAGCUGC AAAGAAAAGA UUUCAGUUCA AGGUCGUUCC CAAUUAUGCU    5280

AUAACCACCC AGGACGCGAU GAAAAACGUC UGGCAAGUUU UAGUUAAUAU UAGAAAUGUG    5340

AAGAUGUCAG CGGGUUUCUG UCCGCUUUCU CUGGAGUUUG UGUCGGUGUG UAUUGUUUAU    5400

AGAAAUAAUA UAAAAUUAGG UUUGAGAGAG AAGAUUACAA ACGUGAGAGA CGGAGGGCCC    5460

AUGGAACUUA CAGAAGAAGU CGUUGAUGAG UUCAUGGAAG AUGUCCCUAU GUCGAUCAGG    5520

CUUGCAAAGU UUCGAUCUCG AACCGGAAAA AAGAGUGAUG UCCGCAAAGG GAAAAAUAGU    5580

AGUAAUGAUC GGUCAGUGCC GAACAAGAAC UAUAGAAAUG UUAAGGAUUU UGGAGGAAUG    5640

AGUUUUAAAA AGAAUAAUUU AAUCGAUGAU GAUUCGGAGG CUACUGUCGC CGAAUCGGAU    5700

UCGUUUUAAA UAUGUCUUAC AGUAUCACUA CUCCAUCUCA GUUCGUGUUC UUGUCAUCAG    5760

CGUGGGCCGA CCCAAUAGAG UUAAUUAAUU UAUGUACUAA UGCCUUAGGA AAUCAGUUUC    5820

AAACACAACA AGCUCGAACU GUCGUUCAAA GACAAUUCAG UGAGGUGUGG AAACCUUCAC    5880

CACAAGUAAC UGUUAGGUUC CCUGACAGUG ACUUUAAGGU GUACAGGUAC AAUGCGGUAU    5940

UAGACCCGCU AGUCACAGCA CUGUUAGGUG CAUUCGACAC UAGAAAUAGA AUAAUAGAAG    6000

UUGAAAAUCA GGCGAACCCC ACGACUGCCG AAACGUUAGA UGCUACUCGU AGAGUAGACG    6060

ACGCAACGGU GGCCAUAAGG AGCGCGAUAA AUAAUUUAAU AGUAGAAUUG AUCAGAGGAA    6120

CCGGAUCUUA UAAUCGGAGC UCUUUCGAGA GCUCUUCUGG UUUGGUUUGG ACCUCUGGUC    6180

CUGCAACCUA GCAAUUACAA GGUCCAGGUG CCCCAGGGG GCCUGGGGCU CCUCAGGGCC    6240

CCGGAGCACC CCAAGGACCG GGCGCGCCCU AGGUAGUCAA GAUGCAUAAU AAAUAACGGA    6300

UUGUGUCCGU AAUCACACGU GGUGCGUACG AUAACGCAUA GUGUUUUUCC CUCCACUUAA    6360

AUCGAAGGGU UGUGUCUUGG AUCGCGCGGG UCAAUGUAUU AUGGUUCAUA UACAUCCGCA    6420

GGCACGUAAU AAAGCGAGGG UUCGAAUCC CCCCGUUACC CCCGGUAGGG GCCCA         6475
```

(2) INFORMATION FOR SEQ ID NO:5:

(i) SEQUENCE CHARACTERISTICS:
        (A) LENGTH: 6446 base pairs
        (B) TYPE: nucleic acid
        (C) STRANDEDNESS: single
        (D) TOPOLOGY: unknown (ii) MOLECULE TYPE: Genomic RNA (xi) SEQUENCE DESCRIPTION: SEQ ID NO:5:

```
GUAUUUUUAC AACAAUUACC AACAACAACA AACAACAAAC AACAUUACAA UUACUAUUUA      60

CAAUUACAAU GGCAUACACA CAGACAGCUA CCACAUCAGC UUUGCUGGAC ACUGUCCGAG     120

GAAACAACUC CUUGGUCAAU GAUCUAGCAA AGCGUCGUCU UUACGACACA GCGGUUGAAG     180

AGUUUAACGC UCGUGACCGC AGGCCCAAGG UGAACUUUUC AAAAGUAAUA AGCGAGGAGC     240

AGACGCUUAU UGCUACCCGG GCGUAUCCAG AAUUCCAAAU UACAUUUUAU AACACGCAAA     300

AUGCCGUGCA UUCGCUUGCA GGUGGAUUGC GAUCUUUAGA ACUGGAAUAU CUGAUGAUGC     360

AAAUUCCCUA CGGAUCAUUG ACUUAUGACA UAGGCGGGAA UUUUGCAUCG CAUCUGUUCA     420
```

```
AGGGACGAGC AUAUGUACAC UGCUGCAUGC CCAACCUGGA CGUUCGAGAC AUCAUGCGGC    480

ACGAAGGCCA GAAAGACAGU AUUGAACUAU ACCUUUCUAG GCUAGAGAGA GGGGGGAAAA    540

CAGUCCCCAA CUUCCAAAAG GAAGCAUUUG ACAGAUACGC AGAAAUUCCU GAAGACGCUG    600

UCUGUCACAA UACUUUCCAG ACAAUGCGAC AUCAGCCGAU GCAGCAAUCA GGCAGAGUGU    660

AUGCCAUUGC GCUACACAGC AUAUAUGACA UACCAGCCGA UGAGUUCGGG GCGGCACUCU    720

UGAGGAAAAA UGUCCAUACG UGCUAUGCCG CUUUCCACUU CUCUGAGAAC CUGCUUCUUG    780

AAGAUUCAUA CGUCAAUUUG GACGAAAUCA ACGCGUGUUU UUCGCGCGAU GGAGACAAGU    840

UGACCUUUUC UUUUGCAUCA GAGAGUACUC UUAAUUAUUG UCAUAGUUAU UCUAAUAUUC    900

UUAAGUAUGU GUGCAAAACU UACUUCCCGG CCUCUAAUAG AGAGGUUUAC AUGAAGGAGU    960

UUUUAGUCAC CAGAGUUAAU ACCUGGUUUU GUAAGUUUUC UAGAAUAGAU ACUUUUCUUU   1020

UGUACAAAGG UGUGGCCCAU AAAAGUGUAG AUAGUGAGCA GUUUUAUACU GCAAUGGAAG   1080

ACGCAUGGCA UUACAAAAAG ACUCUUGCAA UGUGCAACAG CGAGAGAAUC CUCCUUGAGG   1140

AUUCAUCAUC AGUCAAUUAC UGGUUUCCCA AAAUGAGGGA UAUGGUCAUC GUACCAUUAU   1200

UCGACAUUUC UUUGGAGACU AGUAAGAGGA CGCGCAAGGA AGUCUUAGUG UCCAAGGAUU   1260

UCGUGUUUAC AGUGCUUAAC CACAUUCGAA CAUACCAGGC GAAAGCUCUU ACAUACGCAA   1320

AUGUUUUGUC CUUUGUCGAA UCGAUUCGAU CGAGGGUAAU CAUUAACGGU GUGACAGCGA   1380

GGUCCGAAUG GGAUGUGGAC AAAUCUUUGU UACAAUCCUU GUCCAUGACG UUUUACCUGC   1440

AUACUAAGCU UGCCGUUCUA AAGGAUGACU UACUGAUUAG CAAGUUUAGU CUCGGUUCGA   1500

AAACGUGUGU CCAGCAUGUG UGGGAUGAGA UUUCGCUGGC GUUUGGGAAC GCAUUCCCCU   1560

CCGUGAAAGA GAGGCUCUUG AACAGGAAAC UUAUCAGAGU GGCAGGCGAC GCAUUAGAGA   1620

UCAGGGUGCC UGAUCUAUAU GUGACCUUCC ACGACAGAUU AGUGACUGAG UACAAGGCCU   1680

CUGUGGACAU GCCUGCGCUU GACAUUAGGA AGAAGAUGGA AGAAACGAA GUGAUGUACA    1740

AUGCACUUUC AGAGUUAUCG GUGUUAAGGG AGUCUGACAA AUUCGAUGUU GAUGUUUUUU   1800

CCCAGAUGUG CCAAUCUUUG GAAGUUGACC CAAUGACGGC AGCGAAGGUU AUAGUCGCGG   1860

UCAUGAGCAA UGAGAGCGGU CUGACUCUCA CAUUUGAACG ACCUACUGAG GCGAAUGUUG   1920

CGCUAGCUUU ACAGGAUCAA GAGAAGGCUU CAGAAGGUGC UUUGGUAGUU ACCUCAAGAG   1980

AAGUUGAAGA ACCGUCCAUG AAGGGUUCGA UGGCCAGAGG AGAGUUACAA UUAGCUGGUC   2040

UUGCUGGAGA UCAUCCGGAG UCGUCCUAUU CUAAGAACGA GGAGAUAGAG UCUUUAGAGC   2100

AGUUUCAUAU GGCAACGGCA GAUUCGUUAA UUCGUAAGCA GAUGAGCUCG AUUGUGUACA   2160

CGGGUCCGAU UAAAGUUCAG CAAAUGAAAA ACUUUAUCGA UAGCCUGGUA GCAUCACUAU   2220

CUGCUGCGGU GUCGAAUCUC GUCAAGAUCC UCAAAGAUAC AGCUGCUAUU GACCUUGAAA   2280

CCCGUCAAAA GUUUGGAGUC UUGGAUGUUG CAUCUAGGAA GUGGUUAAAUC AAACCAACGG   2340

CCAAGAGUCA UGCAUGGGGU GUUGUUGAAA CCCACGCGAG GAAGUAUCAU GUGGCGCUUU   2400

UGGAAUAUGA UGAGCAGGGU GUGGUGACAU GCGAUGAUUG GAGAAGAGUA GCUGUCAGCU   2460

CUGAGUCUGU UGUUUAUUCC GACAUGGCGA AACUCAGAAC UCUGCGCAGA CUGCUUCGAA   2520

ACGGAGAACC GCAUGUCAGU AGCGCAAAGG UUGUUCUUGU GGACGGAGUU CCGGGCUGUG   2580

GGAAAACCAA AGAAAUUCUU UCCAGGGUUA AUUUUGAUGA AGAUCUAAUU UUAGUACCUG   2640

GGAAGCAAGC CGCGGAAAUG AUCAGAAGAC GUGCGAAUUC CUCAGGGAUU AUUGUGGCCA   2700

CGAAGGACAA CGUUAAAACC GUUGAUUCUU UCAUGAUGAA UUUUGGGAAA GCACACGCU    2760

GUCAGUUCAA GAGGUUAUUC AUUGAUGAAG GGUUGAUGUU GCAUACUGGU UGUGUUAAUU   2820
```

```
UUCUUGUGGC GAUGUCAUUG UGCGAAAUUG CAUAUGUUUA CGGAGACACA CAGCAGAUUC    2880

CAUACAUCAA UAGAGUUUCA GGAUUCCCGU ACCCCGCCCA UUUUGCCAAA UUGGAAGUUG    2940

ACGAGGUGGA GACACGCAGA ACUACUCUCC GUUGUCCAGC CGAUGUCACA CAUUAUCUGA    3000

ACAGGAGAUA UGAGGGCUUU GUCAUGAGCA CUUCUUCGGU UAAAAAGUCU GUUUCGCAGG    3060

AGAUGGUCGG CGGAGCCGCC GUGAUCAAUC CGAUCUCAAA ACCCUUGCAU GGCAAGAUCC    3120

UGACUUUUAC CCAAUCGGAU AAAGAAGCUC UGCUUUCAAG AGGGUAUUCA GAUGUUCACA    3180

CUGUGCAUGA AGUGCAAGGC GAGACAUACU CUGAUGUUUC ACUAGUUAGG UUAACCCCUA    3240

CACCAGUCUC CAUCAUUGCA GGAGACAGCC CACAUGUUUU GGUCGCAUUG UCAAGGCACA    3300

CCUGUUCGCU CAAGUACUAC ACUGUUGUUA UGGAUCCUUU AGUUAGUAUC AUUAGAGAUC    3360

UAGAGAAACU UAGCUCGUAC UUGUUAGAUA UGUAUAAGGU CGAUGCAGGA ACACAAUAGC    3420

AAUUACAGAU UGACUCGGUG UUCAAAGGUU CCAAUCUUUU UGUUGCAGCG CCAAAGACUG    3480

GUGAUAUUUC UGAUAUGCAG UUUUACUAUG AUAAGUGUCU CCCAGGCAAC AGCACCAUGA    3540

UGAAUAAUUU UGAUGCUGUU ACCAUGAGGU UGACUGACAU UUCAUUGAAU GUCAAAGAUU    3600

GCAUAUUGGA UAUGUCUAAG UCUGUUGCUG CGCCUAAGGA UCAAAUCAAA CCACUAAUAC    3660

CUAUGGUACG AACGGCGGCA GAAAUGCCAC GCCAGACUGG ACUAUUGGAA AAUUUAGUGG    3720

CGAUGAUUAA AAGGAACUUU AACGCACCCG AGUUGUCUGG CAUCAUUGAU AUUGAAAAUA    3780

CUGCAUCUUU AGUUGUAGAU AAGUUUUUUG AUAGUUAUUU GCUUAAAGAA AAAAGAAAAC    3840

CAAAUAAAAA UGUUUCUUUG UUCAGUAGAG AGUCUCUCAA UAGAUGGUUA GAAAAGCAGG    3900

AACAGGUAAC AAUAGGCCAG CUCGCAGAUU UUGAUUUUGU AGAUUUGCCA GCAGUUGAUC    3960

AGUACAGACA CAUGAUUAAA GCACAACCCA AGCAAAAAUU GGACACUUCA AUCCAAACGG    4020

AGUACCCGGC UUUGCAGACG AUUGUGUACC AUUCAAAAAA GAUCAAUGCA UAUUUGGCC    4080

CGUUGUUUAG UGAGCUUACU AGGCAAUUAC UGGACAGUGU UGAUUCGAGC AGAUUUUUGU    4140

UUUUCACAAG AAAGACACCA GCGCAGAUUG AGGAUUUCUU CGGAGAUCUC GACAGUCAUG    4200

UGCCGAUGGA UGUCUUGGAG CUGGAUAUAU CAAAAUACGA CAAAUCUCAG AAUGAAUUCC    4260

ACUGUGCAGU AGAAUACGAG AUCGGCGAA GAUUGGGUUU UGAAGACUUC UUGGGAGAAG    4320

UUUGGAAACA AGGGCAUAGA AAGACCACCC UCAAGGAUUA UACCGCAGGU AUAAAAACUU    4380

GCAUCUGGUA UCAAAGAAAG AGCGGGACG UCACGACGUU CAUUGGAAAC ACUGUGAUCA    4440

UUGCUGCAUG UUUGGCCUCG AUGCUUCCGA UGGAGAAAAU AAUCAAAGGA GCCUUUUGCG    4500

GUGACGAUAG UCUGCUGUAC UUUCCAAAGG GUUGUGAGUU CCGGAUGUG CAACACUCCG    4560

CGAAUCUUAU GUGGAAUUUU GAAGCAAAAC UGUUUAAAAA ACAGUAUGGA UACUUUUGCG    4620

GAAGAUAUGU AAUACAUCAC GACAGAGGAU GCAUUGUGUA UUACGAUCCC CUAAAGUUGA    4680

UCUCGAAACU UGGUGCUAAA CACAUCAAGG AUUGGGAACA CUGGAGGAG UUCAGAAGGU    4740

CUCUUUGUGA UGUUGCUGUU CGUUGAACA AUUGUGCGUA UUACACACAG UUGGACGACG    4800

CUGUAUGGGA GGUUCAUAAG ACCGCCCCUC CAGGUUCGUU UGUUUAUAAA AGUCUGGUGA    4860

AGUAUUUGUC UGAUAAAGUU CUUUUUAGAA GUUUGUUUAU AGAUGGCUCU AGUUGUUAAA    4920

GGAAAAGUGA AUAUCAAUGA GUUUAUCGAC CUGACAAAAA UGGAGAAGAU CUUACCGUCG    4980

AUGUUUACCC CUGUAAAGAG UGUUAUGUGU UCCAAAGUUG AUAAAAUAAU GGUUCAUGAG    5040

AAUGAGUCAU UGUCAGAGGU GAACCUUCUU AAAGGAGUUA AGCUUAUUGA UAGUGGAUAC    5100

GUCUGUUUAG CCGGUUUGGU CGUCACGGGC GAGUGGAACU UGCCUGACAA UUGCAGAGGA    5160
```

-continued

| | | | | | |
|---|---|---|---|---|---|
| GGUGUGAGCG | UGUGUCUGGU | GGACAAAAGG | AUGGAAAGAG | CCGACGAGGC | CACUCUCGGA 5220 |
| UCUUACUACA | CAGCAGCUGC | AAAGAAAAGA | UUUCAGUUCA | AGGUCGUUCC | CAAUUAUGCU 5280 |
| AUAACCACCC | AGGACGCGAU | GAAAAACGUC | UGGCAAGUUU | UAGUUAAUAU | UAGAAAUGUG 5340 |
| AAGAUGUCAG | CGGGUUUCUG | UCCGCUUUCU | CUGGAGUUUG | UGUCGGUGUG | UAUUGUUUAU 5400 |
| AGAAAUAAUA | UAAAAUUAGG | UUUGAGAGAG | AAGAUUACAA | ACGUGAGAGA | CGGAGGGCCC 5460 |
| AUGGAACUUA | CAGAAGAAGU | CGUUGAUGAG | UUCAUGGAAG | AUGUCCCUAU | GUCGAUCAGG 5520 |
| CUUGCAAAGU | UUCGAUCUCG | AACCGGAAAA | AAGAGUGAUG | UCCGCAAAGG | GAAAAAUAGU 5580 |
| AGUAAUGAUC | GGUCAGUGCC | GAACAAGAAC | UAUAGAAAUG | UUAAGGAUUU | UGGAGGAAUG 5640 |
| AGUUUUAAAA | AGAAUAAUUU | AAUCGAUGAU | GAUUCGGAGG | CUACUGUCGC | CGAAUCGGAU 5700 |
| UCGUUUUAAA | UAUGUCUUAC | AGUAUCACUA | CUCCAUCUCA | GUUCGUGUUC | UUGUCAUCAG 5760 |
| CGUGGGCCGA | CCCAAUAGAG | UUAAUUAAUU | UAUGUACUAA | UGCCUUAGGA | AAUCAGUUUC 5820 |
| AAACACAACA | AGCUCGAACU | GUCGUUCAAA | GACAAUUCAG | UGAGGUGUGG | AAACCUUCAC 5880 |
| CACAAGUAAC | UGUUAGGUUC | CCUGACAGUG | ACUUUAAGGU | GUACAGGUAC | AAUGCGGUAU 5940 |
| UAGACCCGCU | AGUCACAGCA | CUGUUAGGUG | CAUUCGACAC | UAGAAAUAGA | AUAAUAGAAG 6000 |
| UUGAAAAUCA | GGCGAACCCC | ACGACUGCCG | AAACGUUAGA | UGCUACUCGU | AGAGUAGACG 6060 |
| ACGCAACGGU | GGCCAUAAGG | AGCGCGAUAA | AUAAUUUAAU | AGUAGAAUUG | AUCAGAGGAA 6120 |
| CCGGAUCUUA | UAAUCGGAGC | UCUUUCGAGA | GCUCUUCUGG | UUUGGUUUGG | ACGUCUGGGC 6180 |
| CGGCAUCAUA | GCAAUUAAUG | AUCCUUCCAU | GGAAGUGGCC | UUGGUGGCCA | UGGCGCCGAU 6240 |
| GAGGUAGUCA | AGAUGCAUAA | UAAAUAACGG | AUUGUGUCCG | UAAUCACACG | UGGUGCGUAC 6300 |
| GAUAACGCAU | AGUGUUUUUC | CCUCCACUUA | AAUCGAAGGG | UUGUGUCUUG | GAUCGCGCGG 6360 |
| GUCAAAUGUA | UAUGGUUCAU | AUACAUCCGC | AGGCACGUAA | UAAAGCGAGG | GGUUCGAAUC 6420 |
| CCCCCGUUAC | CCCCGGUAGG | GGCCCA | | | 6446 |